US007888038B2

(12) United States Patent
Kiefer et al.

(10) Patent No.: US 7,888,038 B2
(45) Date of Patent: Feb. 15, 2011

(54) BAK BINDING PROTEIN, DNA ENCODING THE PROTEIN, AND METHODS OF USE THEREOF

(75) Inventors: Michael C. Kiefer, Clayton, CA (US); Paul A. Fitzpatrick, Albany, CA (US); Helen L. Gibson, Oakland, CA (US); Philip J. Barr, Oakland, CA (US)

(73) Assignee: Genetech, Inc., South San Francisco, CA (US)

( * ) Notice: Subject to any disclaimer, the term of this patent is extended or adjusted under 35 U.S.C. 154(b) by 484 days.

(21) Appl. No.: 11/539,859

(22) Filed: Oct. 9, 2006

(65) Prior Publication Data

US 2007/0099215 A1 May 3, 2007

Related U.S. Application Data

(63) Continuation of application No. 10/189,294, filed on Jul. 1, 2002, now Pat. No. 7,316,915, which is a continuation of application No. 09/381,488, filed as application No. PCT/US98/04079 on Mar. 3, 1998, now Pat. No. 6,441,135.

(60) Provisional application No. 60/041,328, filed on Mar. 20, 1997, provisional application No. 60/071,097, filed on Jan. 9, 1998.

(51) Int. Cl.
*G01N 33/53* (2006.01)
(52) U.S. Cl. .................... 435/7.1; 435/320.1; 435/252; 435/325; 435/69.1; 530/350
(58) Field of Classification Search ................ None
See application file for complete search history.

(56) References Cited

U.S. PATENT DOCUMENTS 5,656,725 A * 8/1997 Chittenden et al. .......... 530/324
5,914,249 A 6/1999 Lal et al. .................. 435/69.1
6,221,615 B1 * 4/2001 Chittenden et al. .......... 435/7.1

FOREIGN PATENT DOCUMENTS

WO WO 93/11267 7/1993
WO WO 95/15084 6/1995
WO WO 96/33416 10/1996

OTHER PUBLICATIONS

Bonaldo et al., *Genome Research*, 6: 791-806 (1996).
Chittenden et al., *Nature*, 374:733-736 (1995).
Guo et al., *Biochemistry*, 101: 9205-9210 (2004).
Kiefer et al., *Nature*, 374:736-739 (1995).
Oudejans et al., *Blood*, 86(5):1893-1902 (1995).
Pearson et al., *Virology*, 160:151-161 (1987).
Seffernick et al., *Journal of Bacteriology* 183: 2405-2410 (2001).
Wells, *Biochemistry* 29: 8517-8521 (1990).
Suzuki, N, GenBank Accession No. D38490 (1994).
Wilson, RK, GenBank Accession No. H21199 (1995).
Wilson, RK, GenBank Accession No. H39163 (1995).
Wilson, RK, GenBank Accession No. H43518 (1995).
Wilson, RK, GenBank Accession No. H49123 (1995).
Wilson, RK, GenBank Accession No. T68394 (1995).
Hillier, L, et al., GenBank Accession No. T78543 (1995).

* cited by examiner

*Primary Examiner*—Hope A Robinson
(74) *Attorney, Agent, or Firm*—Sheridan Ross, P.C.

(57) ABSTRACT

The present invention provide polynucleotide sequences encoding a Bak Binding Protein (BBP) and fragments thereof that bind to Bak. The invention also provide recombinant host cells containing polynucleotides encoding BBP. The invention further provide antibodies that specifically bind to BBP. The invention further provide methods for detecting agents such as drugs that alter the binding of a BBP with a Bak protein. The invention further provide methods for detecting the presence of Bak polynucleotides and the encoding proteins in a biological sample, and further provide methods for modulating the levels of BBP in a cell. This invention additionally encompasses novel peptides, designated the "BBP Binding Domains" and the respective nucleotides, designated "bbpbd-1" and "bbpbd-2" which are involved in the interaction between Bak and BBP.

15 Claims, 11 Drawing Sheets

Figure 2A

SEQ ID NO.: 1

```
                                                                >Aha2
         10         20         30         40         50 |       60         70         80
          *          *          *          *          *          *          *          *
GAGGATCTAC AGGGGACAAG TAAAGGCTAC ATCCAGATGC CGGGAATGCA CTGACGCCCA TTCCTGGAAA CTGGGCTCCC
CTCCTAGATG TCCCCTGTTC ATTTCCGATG TAGGTCTACG GCCCTTACGT GACTGCGGGT AAGGACCTTT GACCCGAGGG
                                                                      >SmaI         >BamH1
         90        100        110        120        130        140  |   150    |   160
          *          *          *          *          *          *          *      |  *
ACTCAGCCCC TGGGAGCAGC AGCCGCCAGC CCCTCGGACC TCCATCTCCA CCCTGCTGAG CCACCCGGGT TGGGCCAGGA
TGAGTCGGGG ACCCTCGTCG TCGGCGGTCG GGGAGCCTGG AGGTAGAGGT GGGACGACTC GGTGGGCCCA ACCCGGTCCT
                      >BsaI
        170        180  |     190        200        210        220        230
          *          *          *          *          *          *          *
TCCCGGCAGG CTGATCCCGT CCTCCACTGA GACCTGAAAA ATG GCT TCG GGG CAA GGC CCA GGT CCT CCC AGG
AGGGCCGTCC GACTAGGGCA GGAGGTGACT CTGGACTTTT TAC CGA AGC CCC GTT CCG GGT CCA GGA GGG TCC
                                                M   A   S   G   Q   G   P   G   P   P   R>

240        250        260        270        280        290
          *          *          *          *          *          *
CAG GAG TGC GGA GAG CCT GCC CTG CCC TCT GCT TCT GAG GAG CAG GTA GCC CAG GAC ACA GAG GAG
GTC CTC ACG CCT CTC GGA CGG GAC GGG AGA CGA AGA CTC CTC GTC CAT CGG GTC CTG TGT CTC CTC
 Q   E   C   G   E   P   A   L   P   S   A   S   E   E   Q   V   A   Q   D   T   E   E>

300        310        320        330        340        350        360
  *          *          *          *          *          *          *
GTT TTC CGC AGC TAC GTT TTT TAC CGC CAT CAG CAG GAA CAG GAG GCT GAA GGG GTG GCT GCC CCT
CAA AAG GCG TCG ATG CAA AAA ATG GCG GTA GTC GTC CTT GTC CTC CGA CTT CCC CAC CGA CGG GGA
 V   F   R   S   Y   V   F   Y   R   H   Q   Q   E   Q   E   A   E   G   V   A   A   P>

>NcoI
        370        380        390        400        410|       420        430
          *          *          *          *          *|         *          *
GCC GAC CCA GAG ATG GTC ACC TTA CCT CTG CAA CCT AGC AGC ACC ATG GGG CAG GTG GGA CGG CAG
CGG CTG GGT CTC TAC CAG TGG AAT GGA GAC GTT GGA TCG TCG TGG TAC CCC GTC CAC CCT GCC GTC
 A   D   P   E   M   V   T   L   P   L   Q   P   S   S   T   M   G   Q   V   G   R   Q>

440        450        460        470        480        490
          *          *          *          *          *          *
CTC GCC ATC ATC GGG GAC GAC ATC AAC CGA CGC TAT GAC TCA GAG TTC CAG ACC ATG TTG CAG CAC
GAG CGG TAG TAG CCC CTG CTG TAG TTG GCT GCG ATA CTG AGT CTC AAG GTC TGG TAC AAC GTC GTG
 L   A   I   I   G   D   D   I   N   R   R   Y   D   S   E   F   Q   T   M   L   Q   H>

>PstI                        >ScaI
500 |      510        520       |530        540        550        560
  *|         *          *        |*          *          *          *
CTG CAG CCC ACG GCA GAG AAT GCC TAT GAG TAC TTC ACC AAG ATT GCC ACC AGC CTG TTT GAG AGT
GAC GTC GGG TGC CGT CTC TTA CGG ATA CTC ATG AAG TGG TTC TAA CGG TGG TCG GAC AAA CTC TCA
 L   Q   P   T   A   E   N   A   Y   E   Y   F   T   K   I   A   T   S   L   F   E   S>

570        580        590        600        610        620
          *          *          *          *          *          *
GGC ATC AAT TGG GGC CGT GTG GTG GCT CTT CTG GGC TTC GGC TAC CGT CTG GCC CTA CAC GTC TAC
CCG TAG TTA ACC CCG GCA CAC CAC CGA GAA GAC CCG AAG CCG ATG GCA GAC CGG GAT GTG CAG ATG
 G   I   N   W   G   R   V   V   A   L   L   G   F   G   Y   R   L   A   L   H   V   Y>

>SalI
630        640        650        660        670      |  680        690
  *          *          *          *          *          *          *
CAG CAT GGC CTG ACT GGC TTC CTA GGC CAG GTG ACC CGC TTC GTG GTC GAC TTC ATG CTG CAT CAC
GTC GTA CCG GAC TGA CCG AAG GAT CCG GTC CAC TGG GCG AAG CAC CAG CTG AAG TAC GAC GTA GTG
 Q   H   G   L   T   G   F   L   G   Q   V   T   R   F   V   V   D   F   M   L   H   H>

700        710        720        730        740        750        760
          *          *          *          *          *          *          *
TGC ATT GCC CGG TGG ATT GCA CAG AGG GGT GGC TGG GTG GCA GCC CTG AAC TTG GGC AAT GGT CCC
ACG TAA CGG GCC ACC TAA CGT GTC TCC CCA CCG ACC CAC CGT CGG GAC TTG AAC CCG TTA CCA GGG
 C   I   A   R   W   I   A   Q   R   G   G   W   V   A   A   L   N   L   G   N   G   P>

770        780        790        800        810        820
          *          *          *          *          *          *
ATC CTG AAC GTG CTG GTG GTT CTG GGT GTG GTT CTG TTG GGC CAG TTT GTG GTA CGA AGA TTC TTC
TAG GAC TTG CAC GAC CAC CAA GAC CCA CAC CAA GAC AAC CCG GTC AAA CAC CAT GCT TCT AAG AAG
 I   L   N   V   L   V   V   L   G   V   V   L   L   G   Q   F   V   V   R   R   F   F>
```

Figure 2B

```
                                                                        >Af12
      830         840         850         860         870         880  |      890         900
       *           *           *           *           *           *           *           *
      AAA TCA TGA CTCC CAAGGGTGCC CTTTGGGTCC CGGTTCAGAC CCCTGCCTGG ACTTAAGCGA AGTCTTTGCC
      TTT AGT ACT GAGG GTTCCCACGG GAAACCCAGG GCCAAGTCTG GGGACGGACC TGAATTCGCT TCAGAAACGG
       K   S   *>

>Hind3
                                                              |
      910         920         930         940         950         960         970         980
       *           *           *           *           *           *           *           *
      TTCTCTGTTC CCTTGCAGGG TCCCCCCTCA AGAGTACAGA AGCTTTAGCA AGTGTGCACT CCAGCTTCGG AGGCCCTGCG
      AAGAGACAAG GGAACGTCCC AGGGGGGAGT TCTCATGTCT TCGAAATCGT TCACACGTGA GGTCGAAGCC TCCGGGACGC >Pst1                                                        >Apa1
                         |                                                            |
      990         1000        1010        1020        1030        1040        1050        1060
       *           *           *           *           *           *           *           *
      TGGGGGCCAG TCAGGCTGCA GAGGCACCTC AACATTGCAT GGTGCTAGTG CCCTCTCTCT GGGCCCAGGG CTGTGGCCGT
      ACCCCCGGTC AGTCCGACGT CTCCGTGGAG TTGTAACGTA CCACGATCAC GGGAGAGAGA CCCGGGTCCC GACACCGGCA 1070        1080        1090        1100        1110        1120        1130        1140
       *           *           *           *           *           *           *           *
      CTCCTCCCTC AGCTCTCTGG GACCTCCTTA GCCCTGTCTG CTAGGCGCTG GGGAGACTGA TAACTTGGGG AGGCAAGAGA
      GAGGAGGGAG TCGAGAGACC CTGGAGGAAT CGGGACAGAC GATCCGCGAC CCCTCTGACT ATTGAACCCC TCCGTTCTCT 1150        1160        1170        1180        1190        1200        1210        1220
       *           *           *           *           *           *           *           *
      CTGGGAGCCA CTTCTCCCCA GAAAGTGTTT AACGGTTTTA GCTTTTTATA ATACCCTTGT GAGAGCCCAT TCCCACCATT
      GACCCTCGGT GAAGAGGGGT CTTTCACAAA TTGCCAAAAT CGAAAAATAT TATGGGAACA CTCTCGGGTA AGGGTGGTAA >Aha2
                     |
      1230         1240       1250        1260        1270        1280        1290        1300
       *           *           *           *           *           *           *           *
      CTACCTGAGG CCAGGACGTC TGGGGTGTGG GGATTGGTGG GTCTATGTTC CCCAGGATTC AGCTATTCTG GAAGATCAGC
      GATGGACTCC GGTCCTGCAG ACCCCACACC CCTAACCACC CAGATACAAG GGGTCCTAAG TCGATAAGAC CTTCTAGTCG 1310        1320        1330        1340        1350        1360        1370        1380
       *           *           *           *           *           *           *           *
      ACCCTAAGAG ATGGACTAG GACCTGAGCC TGGTCCTGGC CGTCCCTAAG CATGTGTCCC AGGAGCAGGA CCTACTAGGA
      TGGGATTCTC TACCCTGATC CTGGACTCGG ACCAGGACCG GCAGGGATTC GTACACAGGG TCCTCGTCCT GGATGATCCT 1390        1400        1410        1420        1430        1440        1450        1460
       *           *           *           *           *           *           *           *
      GAGGGGGGCC AAGGTCCTGC TCAACTCTAC CCCTGCTCCC ATTCCTCCCT CCGGCCATAC TGCCTTTGCA GTTGGACTCT
      CTCCCCCCGG TTCCAGGACG AGTTGAGATG GGGACGAGGG TAAGGAGGGA GGCCGGTATG ACGGAAACGT CAACCTGAGA 1470        1480        1490        1500        1510        1520        1530        1540
       *           *           *           *           *           *           *           *
      CAGGGATTCT GGGCTTGGGG TGTGGGGTGG GGTGGAGTCG CAGACCAGAG CTGTCTGAAC TCACGTGTCA GAAGCCTCCA
      GTCCCTAAGA CCCGAACCCC ACACCCCACC CCACCTCAGC GTCTGGTCTC GACAGACTTG AGTGCACAGT CTTCGGAGGT 1550        1560        1570        1580        1590        1600        1610        1620
       *           *           *           *           *           *           *           *
      AGCCTGCCTC CCAAGGTCCT CTCAGTTCTC TCCCTTCCTC TCTCCTTATA GACACTTGCT CCCAACCCAT TCACTACAGG
      TCGGACGGAG GGTTCCAGGA GAGTCAAGAG AGGGAAGGAG AGAGGAATAT CTGTGAACGA GGGTTGGGTA AGTGATGTCC 1630        1640        1650        1660        1670        1680        1690        1700
       *           *           *           *           *           *           *           *
      TGAAGGCTCT CACCCATCCC TGGGGGCCTT GGGTGAGTGG CCTGCTAAGG CTCCTCCTTG CCCAGACTAC AGGGCTTAGG
      ACTTCCGAGA GTGGGTAGGG ACCCCCGGAA CCCACTCACC GGACGATTCC GAGGAGGAAC GGGTCTGATG TCCCGAATCC 1710        1720        1730        1740        1750        1760        1770        1780
       *           *           *           *           *           *           *           *
      ACTTGGTTTG TTATATCAGG GAAAAGGAGT AGGGAGTTCA TCTGGAGGGT TCTAAGTGGG AGAAGGACTA TCAACACCAC
      TGAACCAAAC AATATAGTCC CTTTTCCTCA TCCCTCAAGT AGACCTCCCA AGATTCACCC TCTTCCTGAT AGTTGTGGTG >BamH1
                        |
      1790         1800       1810        1820        1830        1840        1850        1860
       *           *           *           *           *           *           *           *
      TAGGAATCCC AGAGGTGGAT CCTCCCTCAT GGCTCTGGCA CAGTGTAATC CAGGGGTGTA GATGGGGGAA CTGTGAATAC
      ATCCTTAGGG TCTCCACCTA GGAGGGAGTA CCGAGACCGT GTCACATTAG GTCCCCACAT CTACCCCCTT GACACTTATG
```

Figure 2C

```
                                                           >BsaI
       1870        1880        1890        1900        1910        1920        1930        1940
         *           *           *           *          |*           *           *           *
   TTGAACTCTG  TTCCCCCACC  CTCCATGCTC  CTCACCTGTC  TAGGTCTCCT  CAGGGTGGGG  GGTGACAGTG  CCTTCTCTAT
   AACTTGAGAC  AAGGGGGTGG  GAGGTACGAG  GAGTGGACAG  ATCCAGAGGA  GTCCCACCCC  CCACTGTCAC  GGAAGAGATA 1950        1960        1970        1980        1990        2000        2010        2020
         *           *           *           *           *           *           *           *
   TGGCACAGCC  TAGGGTCTTG  GGGGTCAGGG  GGGAGAAGTT  CTTGATTCAG  CCAAATGCAG  GGAGGGGAGG  CAGATGGAGC
   ACCGTGTCGG  ATCCCAGAAC  CCCCAGTCCC  CCCTCTTCAA  GAACTAAGTC  GGTTTACGTC  CCTCCCCTCC  GTCTACCTCG 2030        2040        2050        2060        2070        2080        2090
         *           *           *           *           *           *           *
   CCATAGGCCA  CCCCCTATCC  TCTGAGTGTT  TGGAAATAAA  CTGTGCAATC  CCCTCAAAAA  AAAAACGGAG  ATCC
   GGTATCCGGT  GGGGGATAGG  AGACTCACAA  ACCTTTATTT  GACACGTTAG  GGGAGTTTTT  TTTTTGCCTC  TAGG
```

Figure 3

SEQ ID NO.: 2

LPLQPSSTMGQVGRQLAIIGDDINRRYDSEFQTMLQHLQPTAENAYEYFTKIATSLFESGNWGRVALLGFGYRLALHVYQHGLTGFLGQVTRFVVDFMLHH
  →Δ2                              Δ3→
CIARWIAQRGGWVAALNLGNGPILNVLVLGVVLLGQFVVRRFFKS
  →ΔTM            ←

MASGQGPGPPRQECGEPALPSASEEQVAQDTEEVFRSYVFYRHQEQEAEGVAAPADPEMVT

Figure 4

SEQ ID NO.: 6

```
                                                gtcctcgcgagacaagctcaccgaa    25
     ATG GCC GCG TCC AGT CAA GGA AAC TTT GAG GGA AAT TTT GAG TCA           70
  1   M   A   A   S   S   Q   G   N   F   E   G   N   F   E   S
     CTG GAC CTT GCG GAA TTT GCT AAG AAG CAG CCA TGG TGG CGT AAG          115
 16   L   D   L   A   E   F   A   K   K   Q   P   W   W   R   K
     CTG TTC GGG CAG GAA TCT GGA CCT TCA GCA GAA AAG TAT AGC GTG          160
 31   L   F   G   Q   E   S   G   P   S   A   E   K   Y   S   V
     GCA ACC CAG CTG TTC ATT GGA GGT GTC ACT GGA TGG TGC ACA GGT          205
 46   A   T   Q   L   F   I   G   G   V   T   G   W   C   T   G
     TTC ATA TTC CAG AAG GTT GGA AAG TTG GCT GCA ACA GCT GTG GGA          250
 61   F   I   F   Q   K   V   G   K   L   A   A   T   A   V   G
     GGT GGA TTT TTT CTC CTT CAG CTT GCA AAC CAT ACT GGG TAC ATC          295
 76   G   G   F   F   L   L   Q   L   A   N   H   T   G   Y   I
     AAA GTT GAC TGG CAA CGA GTG GAG AAG GAC ATG AAG AAA GCC AAA          340
 91   K   V   D   W   Q   R   V   E   K   D   M   K   K   A   K
     GAG CAG CTG AAG ATC CGT AAG AGC AAT CAG ATA CCT ACT GAG GTC          385
106   E   Q   L   K   I   R   K   S   N   Q   I   P   T   E   V
     AGG AGC AAA GCT GAG GAG GTG GTG TCA TTT GTG AAG AAG AAT GTT          430
121   R   S   K   A   E   E   V   V   S   F   V   K   K   N   V
     CTA GTA ACT GGG GGA TTT TTC GGA GGC TTT CTG CTT GGC ATG GCA          475
136   L   V   T   G   G   F   F   G   G   F   L   L   G   M   A
     TCC TAA ggaagatgacctcatgttcattgttcctggttttttccagccagcagcctc          532
151   S   .*
     tacactccatcataggacatcgagtccctcctcctcttctcccatgcccttcttccctgc        592
     catggcaaatctgagtggcttctctaagcatctgctggtacaagtcaatgtggcaccatg        652
     agcttcatggtggcagaagagacaatagtccttagctctcctcccagtacaccccctact        712
     tggccagtctgtaggccaacaagaaggttcctttaccccatgcaagacacttatgagaa         772
     cacattacaagatggctgaccgtggaggatgagtggatcctgaaaggttgtcccaaactg        832
     ttgatttggaaaagaaataagcacatagataaccttattgtgtgctgcatggaaaggaaa        892
     ggaactgaatacatttgcctttaagcatgaaaaaaaaaaaaaaaaaaaaaaaaaaaaaaa        952
     aaaaaaaaaaaaaagaaaaaaa                                              975
```

Figure 6

| AD | BD | | | | | | | | |
|---|---|---|---|---|---|---|---|---|---|
| | BBP | bak | bcl2 | bclx | bax | E1b19k | pLAM5' | pGBT9 |
| BBP | +++ | +++ | - | - | - | - | - | - |
| β-gal units | 32.2 | 20.1 | | 0.05 | | 0.1 | | |

Figure 9

Amino Acids 1-194 of SEQ ID NO.: 2

```
1   MASGQGPGPPRQECGEPALPSASEEQVAQDTEEVFRSYVFYRHQQEQE  48

49  AEGVAAPADPEMVTLPLQPSSTMGQVGRQ LAIIGDDIN RRYDSEFQTML  97
                                   BH3

98  QHLQPTAENAYEYFTKIAT SLFESGINWGRVVALLGFGY RLALHVYQHG  146
                         BH1

147 LTGFLGQVTRFVVDFMLHHCIA RWIAQRGGWVAALNLG NGPILNVLVV  194
                            BH2
```

BAK BINDING PROTEIN, DNA ENCODING THE PROTEIN, AND METHODS OF USE THEREOF

CROSS-REFERENCE TO RELATED APPLICATIONS

This application is a continuation of U.S. patent application Ser. No. 10/189,294, filed Jul. 1, 2002 (now U.S. Pat. No. 7,316,915), which is a continuation of U.S. patent application Ser. No. 09/381,488, filed Feb. 11, 2000 (now U.S. Pat. No. 6,441,135), which is a National Stage entry under 35 U.S.C. §371(c) of PCT/US98/04079, filed Mar. 3, 1998, which claims the benefit of priority under 35 U.S.C. §119 to U.S. provisional patent application Ser. No. 60/071,097, filed Jan. 9, 1998 (now expired) and to U.S. provisional patent application Ser. No. 60/041,328, filed Mar. 20, 1997 (now expired), the entire contents of which are incorporated herein by this reference.

STATEMENT OF RIGHTS TO INVENTIONS MADE UNDER FEDERALLY SPONSORED RESEARCH (Not Applicable)

FIELD OF THE INVENTION

The present invention relates to DNA encoding a protein that binds to a protein involved in apoptosis. The invention further relates to methods for identifying agents that modulate activity levels of a protein binding to a protein involved in apoptosis. The invention additionally encompasses novel peptides, designated the "BBP Binding Domains" which are involved in the interaction between a protein involved in apoptosis and a protein that binds to it.

SUMMARY OF THE INVENTION

Substantially purified DNA encoding a novel Bak binding protein, termed Bak Binding Protein, or BBP, is provided. The substantially purified BBP protein and compositions thereof are also provided. Diagnostic and therapeutic methods utilizing the DNA and proteins are also provided. Methods of screening for pharmaceutical agents that modify Bak and BBP activity levels are also provided. The invention additionally encompasses novel peptides, designated the "BBP Binding Domains" and novel nucleotides, designated "bbpbd-1" and "bbpbd-2" encoding the peptides, which are involved in the interaction between a protein involved in apoptosis and a protein that binds to it.

The present invention encompasses an isolated polypeptide comprising SEQ ID NO:7, isolated polypeptides comprising a linear sequence of six or more amino acids of SEQ ID NO:7, isolated polypeptides having at least one of the biological functions of the polypeptide of SEQ ID NO:7, isolated polypeptides comprising a fragment of SEQ ID NO:7, wherein said fragment binds to Bak protein under appropriate conditions and fusion polypeptides comprising the polypeptide of SEQ ID NO:7 or fragments thereof.

The present invention also encompasses isolated polynucleotides comprising SEQ ID NO:6 and polynucleotide sequences complementary thereto, isolated polynucleotides comprising a fragment of at least 18 consecutive nucleotides of SEQ ID NO:6, isolated polynucleotides encoding the polypeptide of SEQ ID NO:7, isolated polynucleotides comprising a sequence that encodes a polypeptide having at least one of the biological functions of the polypeptide of SEQ ID NO:7 and a polynucleotide complementary thereto, isolated polynucleotides comprising a fragment of SEQ ID NO:6, wherein said fragment encodes a polypeptide that binds to Bak protein under appropriate conditions, and any of the aforementioned isolated polynucleotide, which are operably linked to control sequences for expression.

Also encompassed by the present invention are recombinant vectors comprising any of the aforementioned polynucleotides, as well as recombinant host cells modified to contain the polynucleotides, wherein the recombinant host cells specifically can be bacterial or eukaryotic.

Also encompassed by the present invention are methods for screening potential therapeutic agents that modulate the interaction between Bak and BBP comprising the steps of: (a) combining a Bak and a BBP under conditions in which they interact, to form a test sample; (b) exposing the test sample to a potential therapeutic agent and; (c) monitoring the interaction of the Bak and the BBP; wherein a potential therapeutic agent is selected for further study when it modifies the interaction compared to a control test sample to which no potential therapeutic agent has been added. In one embodiment, the potential therapeutic agent is selected from the group consisting of a pharmaceutical agent, a cytokine, a small molecule drug, a cell-permeable small molecule drug, a hormone, a combination of interleukins, a lectin, a stimulating agent, a bispecific antibody, a peptide mimetic, and an antisense oligonucleotide. In another embodiment, the Bak is selected from the group consisting of Bak, a fragment of Bak sufficient to effect binding to a BBP, and a fusion protein comprising a portion of Bak sufficient to effect binding to a BBP. The fusion protein can comprise epitope-tagged Bak. In one embodiment, the BBP is selected from the group consisting of epitope-tagged BBP and proteins homologous to SEQ ID NO:7. In one embodiment of the present invention, the monitoring step is selected from the group consisting of co-precipitation, protein interactive trapping and ELISA.

The present invention also encompasses compositions comprising a monoclonal or polyclonal antibody or an antigen-binding fragment thereof which forms a complex with a BBP but is substantially unreactive with dissimilar proteins.

The present invention further encompasses a method of detecting the presence of a BBP protein in a biological sample comprising the steps of: a) obtaining a cell sample; b) exposing the contents of the cells to antibodies; c) adding anti-BBP-specific antibodies to the cell sample; d) maintaining the cell sample under conditions that allow the antibodies to complex with the BBP; and e) detecting the antibody-BBP complexes formed.

In one embodiment, a method is provided for detecting the expression of a bbp gene in a biological sample comprising the steps of identifying the presence of RNA encoding the bbp. In one embodiment, identification comprises Northern blotting.

Also encompassed by the present invention are methods identifying bbp mRNA comprising the steps of: (a) obtaining a cell sample; (b) obtaining RNA from the cell sample; (c) performing a polymerase chain reaction on the RNA using primers corresponding to unique regions of bbp; and (d) detecting the presence of products of the polymerase chain reaction.

The present invention also provides methods of modulating apoptosis-induced cell death comprising modulating the endogenous levels of BBP. In a specific embodiment, the BBP levels are increased or decreased by modulating expression of an endogenous bbp gene. In one embodiment, the BBP is encoded by an endogenous gene. Alternatively, the BBP is encoded by a recombinant gene, wherein in a specific embodiment, expression of the recombinant gene is under the control of an inducible promoter. In one embodiment, the recombinant gene is transfected into cells ex vivo and further comprising the steps of reintroducing the transfected cells into an animal. Alternatively, the recombinant gene is transfected into cells in vivo.

The present invention also encompasses methods of inducing apoptosis in a patient in need thereof comprising administering a therapeutically effective amount of the BBP.

The present invention further encompasses isolated polypeptides comprising amino acids 103-126 of SEQ ID NO:2, or derivatives thereof.

Also encompassed are isolated and purified peptides comprising a BBP Binding Domain, isolated polypeptides comprising a linear sequence of six or more amino acids of a BBP Binding Domain, isolated polypeptides having at least one of the biological functions of a BBP Binding Domain, or isolated polypeptides comprising a fragment of a BBP Binding Domain wherein said fragment binds to BBP protein under appropriate conditions. Also encompassed are fusion polypeptides comprising a BBP Binding Domain or fragments thereof.

The present invention further encompasses isolated polynucleotides comprising nucleotides 507-578 of SEQ ID NO:1, and polynucleotide sequences complementary thereto, isolated polynucleotides comprising a fragment of at least 18 consecutive nucleotides of bbpbd-1, isolated polynucleotides comprising nucleotides 611-668 of SEQ ID NO:1, and polynucleotide sequences complementary thereto, isolated polynucleotides comprising a fragment of at least 18 consecutive nucleotides of bbpbd-2, isolated polynucleotides encoding a BBP Binding Domain, isolated polynucleotide comprising a sequence that encodes a polypeptide having at least one of the biological functions of a BBP Binding Domain and a polynucleotide complementary thereto and any of these isolated polynucleotides which is operably linked to control sequences for expression.

In one embodiment, a recombinant vector comprises these polynucleotides. In a specific embodiment, recombinant host cells are modified to contain the polynucleotides. In a specific embodiment, these host cells are bacterial or eukaryotic.

Also encompassed by the present invention are methods of modulating apoptosis-induced cell death comprising modulating the endogenous levels of a BBP Binding Domain, wherein the BBP Binding Domain levels can be increased or decreased by modulating expression of an endogenous bak gene. In alternative embodiments, the BBP Binding Domain is encoded by an endogenous gene or a recombinant gene. In one embodiment, the expression of the recombinant gene is under the control of an inducible promoter. In alternative embodiments, the recombinant gene is transfected into cells ex vivo and further comprising the steps of reintroducing the transfected cells into an animal, or the recombinant gene is transfected into cells in vivo.

Also encompassed by the present invention are methods of modulating apoptosis in a patient in need thereof comprising administering a therapeutically effective amount of a BBP Binding Domain.

The present invention additionally encompasses isolated polypeptides comprising amino acids 138-156 of SEQ ID NO:2, or derivatives thereof.

BACKGROUND

Apoptosis, or programmed cell death, is a normal physiologic process that leads to individual cell death. This process of programmed cell death is involved in a variety of normal and pathogenic biological events and can be induced by a number of unrelated stimuli. Changes in the biological regulation of apoptosis also occur during aging and are responsible for many of the conditions and diseases related to aging. Recent studies of apoptosis have implied that a common metabolic pathway leading to cell death can be initiated by a wide variety of signals, including hormones, serum growth factor deprivation, chemotherapeutic agents, ionizing radiation and infection by human immunodeficiency virus (I-V). Wyllie (1980) *Nature* 284:555-556; Kanter et al. (1984) *Biochem. Biophys. Res. Commun.* 118:392-399; Duke and Cohen (1986) *Lymphokine Res.* 5:289-299; Tomei et al. (1988) *Biochem. Biophys. Res. Commun.* 155:324-331; Kruman et al. (1991) *J. Cell. Physiol.* 148:267-273; Ameisen and Capron (1991) *Immunology Today* 12:102; and Sheppard and Ascher (1992) *J. AIDS* 5:143. Agents that modulate the biological control of apoptosis thus have therapeutic utility in a wide variety of conditions.

Apoptotic cell death is characterized by cellular shrinkage, chromatin condensation, cytoplasmic blebbing, increased membrane permeability and interchromosomal DNA cleavage. Kerr et al. (1992) *FASEB J.* 6:2450; and Cohen and Duke (1992) *Ann. Rev. Immunol.* 10:267.

While apoptosis is a normal cellular event, it can also be induced by pathological conditions and a variety of injuries. Apoptosis is involved in a wide variety of conditions including but not limited to, cardiovascular disease; cancer regression; immune disorders, including but not limited to systemic lupus erythematosus; viral diseases; anemia; neurological disorders; diabetes; hair loss; rejection of organ transplants; prostate hypertrophy; obesity; ocular disorders; stress; aging; and gastrointestinal disorders, including but not limited to, diarrhea and dysentery. In the myocardium, apoptotic cell death follows ischemia and reperfusion.

In Alzheimer's disease, Parkinson's disease, Huntington's chorea, epilepsy, amyotrophic lateral sclerosis, stroke, ischemic heart disease, spinal cord injury and many viral infections, for example, abnormally high levels of cell death occur. In at least some of these diseases, there is evidence that the excessive cell death occurs through mechanisms consistent with apoptosis. Among these are 1) spinal cord injury, where the severing of axons deprives neurons of neurotrophic factors necessary to sustain cellular viability; 2) stroke, where after an initial phase of necrotic cell death due to ischemia, the rupture of dead cells releases excitatory neurotransmitters such as glutamate and oxygen free radicals that stimulate apoptosis in neighboring healthy neurons; and 3) Human Immunodeficiency Virus (HIV) infection, which induces apoptosis of T-lymphocytes.

In contrast, the level of apoptosis is decreased in cancer cells, which allows the cancer cells to survive longer than their normal cell counterparts. As a result of the increased number of surviving cancer cells, the mass of a tumor can increase even if the doubling time of the cancer cells does not increase. Furthermore, the high level of expression in a cancer cell of the bcl-2 gene, which is involved in regulating apoptosis and, in some cases, necrotic cell death, renders the cancer cell relatively resistant to chemotherapeutic agents and to radiation therapy.

In recent years, a family of proteins has been discovered that controls apoptosis. The prototype of this family is Bcl-2, a protein that inhibits most types of apoptotic cell death and is thought to function by regulating an antioxidant pathway at sites of free radical generation. Hockenbery et al. (1993) *Cell* 75:241-251. More recent data suggests that Bcl-2 can also function as a channel protein and as an adaptor/docking protein. Reed, et al. (1997) Nature 387:773-776. Together, the Bcl-2 family of proteins are important intracellular modulators of apoptosis and can be divided into two groups based on their effect on apoptosis. Thus, in a general sense, Bcl-2, Bcl-$x_L$, Mcl-1, BHRF-1 and E1B19K are cell death inhibitors (anti-apoptotic), while Bak, Bax and Bcl-$x_S$ accelerate cell death (pro-apoptotic).

Bcl-2 family members are generally localized to the outer mitochondrial membrane, the nuclear membrane and the endoplasmic reticulum, where they associate with membranes by virtue of their C-terminal hydrophobic tail. All members of the family have two highly conserved regions, called BH1 and BH2, that permit specific interactions between two members to form stable dimers. Their mechanism of action is presently unclear; however, it is known that the ratio of anti-apoptotic to pro-apoptotic Bcl-2 family members in a cell is critical to the cell's survival following initiation of an apoptotic signal.

Proteins that interact with and alter the activity of Bcl-2 have been described. For example, BAG-1 binds Bcl-2, enhances the anti-apoptotic effect of Bcl-2 and furthermore activates Raf-1. Wang et al. (1996) Proc. Natl. Acad. Sci. USA 93:7063-7068; Takayama et al. (1995) Cell 80:279-284. Other proteins with bcl-2 binding activity include the ras-related R-ras p23, BAP and Bad. Fernandez-Sarabia and Bischoff (1993) Nature 366:274-275; U.S. Pat. No. 5,539,085; U.S. Pat. No. 5,539,094; PCT Application WO 96/13614. Identification of such proteins is of great importance, since an understanding of the protein-protein interactions in which apoptosis-related proteins are involved can not only provide insights into the mechanisms of action of these proteins, but can also provide a focal point toward which apoptosis-modulating therapies can be designed. For example, disruption of a protein-protein interaction between an apoptosis-related protein and a protein which enhances its function can decrease the level of apoptosis in a cell. This may be a desired effect in a tissue which displays an inappropriately high level of apoptosis.

Bak is a member of the Bcl-2 family and is expressed in heart and other tissues. Bak protein is capable of either killing cells, or actively protecting cells from cell death, depending on how this protein interacts with other cellular proteins. Bcl-2 family members are extremely important in determining the fate of a cell following an apoptotic signal, and Bak may be the most important in the major organs such as heart. In the treatment of heart disease, viral infection and cancer, modulation of the interactions between proteins that control apoptosis is a major focal point.

Accordingly, there is a need to identify the proteins that operate to control cell death, and to develop therapeutic reagents that modify the actions of those proteins. The present invention relates to a novel Bak binding protein (BBP), the gene encoding the novel protein, methods for detecting substances that alter the specific binding between Bak and BBP, as well as diagnostic and therapeutic methods utilizing BBP. The invention additionally encompasses novel peptides, designated the "BBP Binding Domains" and novel nucleotides, designated "bbpbd-1" and "bbpbd-2" (collectively "bbpbd") encoding the peptides, which are involved in the interaction between a protein involved in apoptosis and a protein that binds to it.

All references cited herein are hereby incorporated by reference in their entirety.

BRIEF DESCRIPTION OF THE DRAWINGS

FIGS. 2A-2C depict the cDNA sequence (SEQ ID NO:1 and 3) of bak and the translated amino acid sequence of Bak (SEQ ID NO:2).

FIG. 3 depicts the Bak (SEQ ID NO:2) derivative proteins BakΔ2-TM (SEQ ID NO:4) and BakΔ3 (SEQ ID NO:5). The N-terminal residues are indicated by rightward arrows. The C-terminus of BakΔ2-TM is indicated by the leftward arrow.

FIG. 4 depicts the cDNA sequence (SEQ ID NO:6) of bbp and the translated amino acid sequence (SEQ ID NO:7) of BBP.

FIG. 6 summarizes the interactions of BBP with other proteins.

FIG. 9 depicts the amino acid sequence of Bak and the regions of Bak that interact with BBP loop 1. Each horizontal line above the amino acid sequence shown indicate locations on the Bak protein where BBP loop1 interacted with a 15 amino acid peptide having the sequence shown directly below the respective line.

MODES OF CARRYING OUT THE INVENTION

Figure 1:
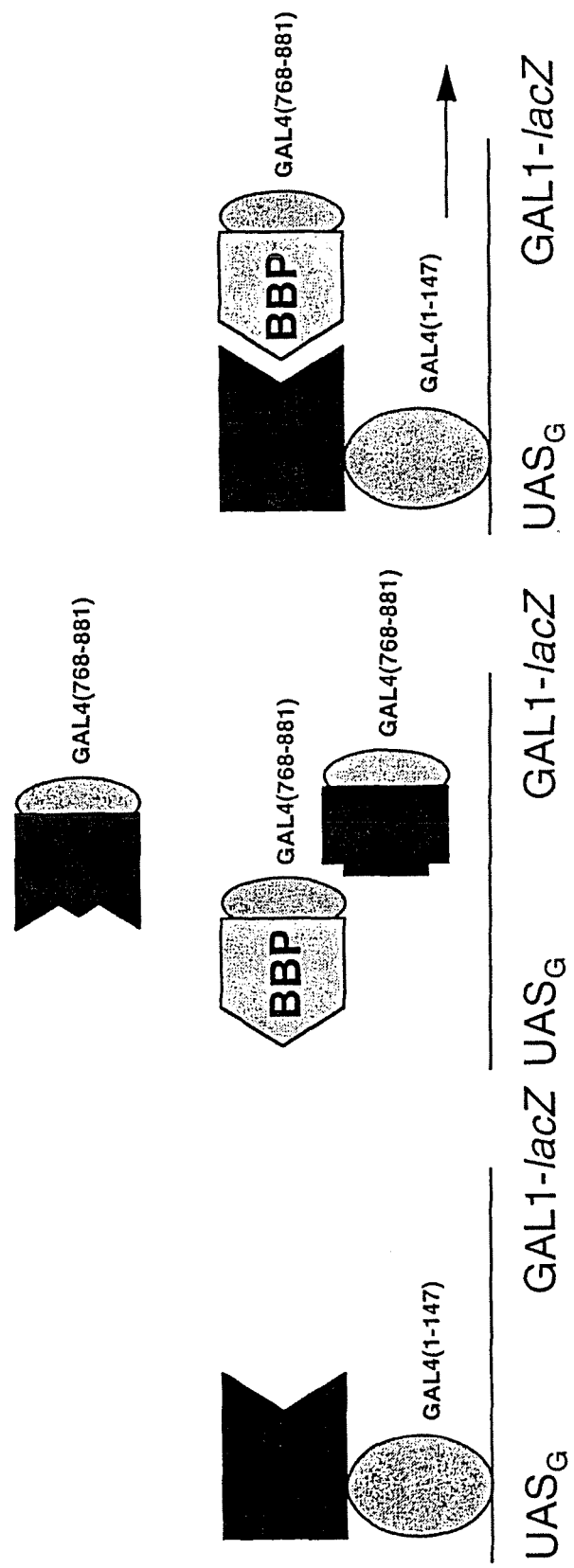
FIG. 1 shows the strategy used to isolate BBP clones.

The present invention encompasses substantially purified nucleotide sequences encoding the novel Bak Binding Protein (BBP); the protein encoded thereby; methods of screening potential therapeutic agents that modify the interaction between BBP and proteins that bind thereto; and methods for detecting substances that alter the specific binding between Bak and BBP. The invention additionally encompasses novel peptides, designated the "BBP Binding Domains" which are involved in the interaction between a protein involved in apoptosis and a protein that binds to it.

The following definitions are for the purpose of clarifying the terms used herein, and are not meant to be limiting. Where definitions or techniques are specified with reference to BBP or bbp, the general teachings provided apply also to BBP Binding Domains or bbpbd, respectively.

The present invention encompasses the polypeptide BBP and modifications of BBP that retain at least one of the biological functions of BBP. The present invention also encompasses the polypeptides BBP Binding Domains and modifications of BBP Binding Domains that retain at least one of the biological functions of BBP Binding Domains. The terms "polypeptide", "peptide" or "protein" are used interchangeably herein. By "polypeptide" is meant a linear sequence of ten or more amino acids.

By "biologically effective amount" and "therapeutically effective amount" is meant a concentration of the component able to improve or ameliorate a condition related to apoptosis.

The term "BBP" encompasses polypeptide and polypeptide fragments of BBP (SEQ ID NO:7) containing at least a portion of BBP that binds to Bak protein or a fragment thereof, or has any other biological or other useful function characteristic of BBP. The term "BBP Binding Domains" encompasses polypeptides and polypeptide fragments of Bak containing at least a portion of Bak protein that binds to BBP or a fragment thereof, or has any other biological or other useful function characteristic of BBP Binding Domains. A BBP is defined primarily by its ability to associate in vitro and in vivo with a Bak protein. A BBP Binding Domain is defined primarily by its ability to associate in vitro and in vivo with BBP. As used herein, "associate" or "interact" or "bind" means that a BBP and a Bak protein have a binding affinity for each other such that the BBP and a Bak protein or BBP Binding Domain form a bound complex. The affinity of binding of a BBP and a Bak protein is sufficiently specific such that the bound complex can form in vivo in a cell and can form in vitro under appropriate conditions, as described herein. The formation or dissociation of a bound complex can be identified as described in the Examples or using other well known methods.

The size of the BBP or BBP Binding Domain polypeptide fragments can be only the minimum size required to provide a desired function. It can optionally comprise additional amino acid sequence, either native to BBP or BBP Binding Domain or from a heterologous source, as desired. BBP or BBP Binding Domain fragments may contain only ten consecutive amino acids from a BBP or BBP Binding Domain amino acid sequence. Polypeptides comprising ten amino acids, more preferably about 15 amino acids, more preferably about 25 amino acids, more preferably about 50 amino acids from the sequence are also included. Even more preferred are polypeptides comprising the entire BBP or BBP Binding Domain amino acid sequence.

The term "BBP" further encompasses a substantially purified preparation of BBP (SEQ ID NO:7), or a fragment of BBP that is an antigenic polypeptide containing from six to 151 amino acid residues of BBP (preferably at least six, more preferably at least 12, and most preferably at least 18), which polypeptide fragment contains an epitope of BBP such that an antibody raised against the fragment (or against a conjugate of the polypeptide and a carrier, including, but not limited to, keyhole limpet hemocyanin) forms an immune complex with BBP itself.

The term "BBP Binding Domain" further encompasses a substantially purified preparation of BBP Binding Domain, or a fragment of BBP that is an antigenic polypeptide containing from six to 23 amino acid residues of a BBP Binding Domain (preferably at least six, more preferably at least 12, and most preferably at least 18), which polypeptide fragment contains an epitope of a BBP Binding Domain such that an antibody raised against the fragment (or against a conjugate of the polypeptide and a carrier, including, but not limited to, keyhole limpet hemocyanin) forms an immune complex with a BBP Binding Domain itself.

Such antibodies can be either monoclonal or polyclonal, and are generated by standard methods including the step of immunizing an animal with an antigen containing an antigenic portion of BBP or BBP Binding Domain.

The terms "BBP" and "BBP Binding Domains" also include modified polypeptides that are functionally equivalent to BBP or BBP Binding Domain, respectively, or fragments thereof. Modifications include addition, insertion or deletion of amino acids. Other examples of modified polypeptides include polypeptides with conservative substitutions in comparison with the prototype BBP or BBP Binding Domain sequence. Substitutions can include changing or modifying one or more amino acids, and insertion of heterologous amino acid sequences. Amino acid substitutions, if present, include conservative substitutions that do not deleteriously affect folding or functional properties of the peptide. Groups of functionally related amino acids within which conservative substitutions can be made are glycine/alanine; valine/isoleucine/leucine; asparagine/glutamine; aspartic acid/glutamic acid; serine/threonine; lysine/arginine; and phenylalanine/tryptophan/tyrosine. Polypeptides of this invention can be modified post-translationally (e.g., acetylation or phosphorylation) or can be modified synthetically (e.g., the attachment of a labeling group).

Some fragments of BBP or BBP Binding Domain or the modified amino acids encompassed by the present invention may lack some biological activities characteristic of native proteins (e.g., binding to Bak or BBP, respectively) but may have activities, and therefor be useful for other purposes, such as for raising antibodies to BBP or BBP Binding Domain epitopes, as an immunological reagent to detect and/or purify BBP or BBP Binding Domain-binding antibodies by affinity chromatography, or as a competitive or noncompetitive agonist, antagonist, or partial agonist of native BBP or BBP Binding Domain protein function.

The invention also encompasses BBP or BBP Binding Domain conjugated to a label capable of producing a detectable signal or other functional moieties. Suitable labels include, but are not limited to, radionuclides, enzymes, substrates, cofactors, inhibitors, fluorescent dyes, chemiluminescent dyes, bioluminescent compounds and magnetic particles. See, for examples of patents teaching the use of such labels, U.S. Pat. Nos. 3,817,837; 3,850,752; 3,939,350; 3,996,345; 4,277,437; 4,275,149; and 4,366,241.

The invention further comprises fusion proteins comprising (1) BBP or BBP Binding Domain or fragments thereof, covalently attached to (2) a second polypeptide. Such fusion polypeptides can be made by any of a number of standard techniques well known to those of ordinary skill, including recombinant methods, in which case the covalent attachment is a peptide bond, or chemical conjugation, in which case the covalent attachment is another type of bond, such as a disulfide bond. A BBP or BBP Binding Domain fusion polypeptide can be prepared, for example, by chemical synthesis, or by creating and translating a polynucleotide in which the peptide regions are encoded in the desired relationship. Useful heterologous sequences for inclusion in a fusion polypeptide include sequences that provide for secretion from a host cell, sequences that enhance immunological reactivity relative to BBP or the BBP fragment, or BBP Binding Domain or the respective fragment, sequences that facilitate the coupling of the polypeptide to an immunoassay support or a vaccine carrier, portions of an immunoglobulin molecule, immunological tags, or sequences that mediate specific binding to a cell surface or intracellular receptor.

The polypeptides described above can be produced in prokaryotic or eukaryotic host cells by expression of polynucleotides encoding the desired peptide sequence. Alternatively, polypeptides can be synthesized by chemical methods.

Purification or isolation of BBP or BBP Binding Domain expressed either by recombinant DNA or from biological sources such as tissues can be accomplished by any method known in the art. Protein purification methods are known in the art. Generally, the terms "substantially purified" or "substantially isolated" or "isolated" are used interchangeably to indicate proteins which are free of other, contaminating cellular substances, particularly proteins. Preferably, the purified BBP or BBP Binding Domain is more than eighty percent pure and most preferably more than ninety-five percent pure.

Suitable methods of protein purification are known in the art and include, but are not limited to, affinity chromatography, immunoaffinity chromatography, size exclusion chromatography, HPLC and FPLC. Any purification scheme that does not result in substantial degradation of the protein is suitable for use in the present invention.

The invention further encompasses isolated polynucleotides (or nucleic acids) encoding polypeptides substantially identical to BBP or BBP Binding Domain or portions thereof. The term polynucleotide as used herein, can be DNA or RNA, either coding or noncoding strands. Similarly "bbp" includes bbp cDNA, genomic DNA and synthetic or semi-synthetic DNAs and RNAs and are additional embodiments of the present invention.

Also included are isolated polynucleotides encoding polypeptides substantially identical to allelic variants of SEQ ID NO:7 or to homologs of BBP or BBP Binding Domain from species other than man. The isolated polynucleotide preferably contains a DNA sequence that hybridizes under stringent conditions (as defined below) with the DNA sequence of SEQ ID NO:6, or the complement thereof, and can contain the sequence of SEQ ID NO:6. It is preferably incorporated into a vector (a virus, phage, or plasmid) which can be introduced by transfection or infection into a cell. The vector preferably includes one or more expression control sequences, in which case the cell transfected by the vector is capable of expressing the polypeptide.

By "isolated nucleotide" is meant a single- or double-stranded nucleotide that is free of the genes which, in the naturally-occurring genome of the animal from which the isolated nucleotide is derived, flank the bbp gene or the bbpbd sequence. The term therefore includes, for example, either or both strands of a cDNA encoding the nucleic acid of interest, or an allelic variant thereof; a recombinant DNA which is incorporated into a vector, into an autonomously replicating plasmid or virus, or into the genomic DNA of a prokaryotic or eukaryotic cell; or a genomic DNA fragment (e.g., produced by PCR (polymerase chain reaction) or restriction endonuclease treatment of human or other genomic DNA). It also includes a recombinant DNA which is part of a hybrid gene encoding additional polypeptide sequence.

Stringent conditions for both DNA/DNA and DNA/RNA hybridization assays are as described by Sambrook et al. *Molecular Cloning, A Laboratory Manual,* 2nd Ed., Cold Spring Harbor Laboratory Press, Cold Spring Harbor, N.Y., 1989, herein incorporated by reference. For example, see page 7.52 of Sambrook et al.

Also within the invention is an isolated DNA at least 15 nucleotides in length (preferably at least 30, more preferably at least 100, and most preferably at least 450), including (a) a strand which hybridizes under stringent conditions to a DNA having the sequence of SEQ ID NO:6, (b) the complement thereof, or (c) a double-stranded DNA including both (a) and (b). Multiple copies of this isolated DNA (useful, for example, as a hybridization probe or PCR primer) can be produced by recombinant means, by transfecting a cell with a vector containing this DNA.

The invention includes modifications to bbp or bbpbd DNA sequences such as deletions, substitutions and additions particularly in the non-coding regions of genomic DNA. Such changes are useful to facilitate cloning and modify gene expression.

Various substitutions can be made within the coding region that either do not alter the amino acid residues encoded or result in conservatively substituted amino acid residues. Nucleotide substitutions that do not alter the amino acid residues encoded are useful for optimizing gene expression in different systems. Suitable substitutions are known to those of skill in the art and are made, for instance, to reflect preferred codon usage in the particular expression systems.

The invention encompasses functionally equivalent variants and derivatives of bbp or bbpbd, which may enhance, decrease or not significantly affect the properties of BBP or BBP Binding Domain, respectively. "Derivatives" are defined herein as changes in the DNA sequence that do not change the encoded amino acid sequence, as well as those that result in conservative substitutions of amino acid residues, one or a few amino acid deletions or additions, and substitution of amino acid residues by amino acid analogs are those which will not significantly affect its properties.

The above-mentioned polynucleotides can include control sequences that facilitate transcription (expression sequences) and translation of the coding sequences, such that the encoded polypeptide product is produced. Such control sequences include, but are not limited to, promoters, transcription termination sites, polyadenylation sites, ribosome binding sites, enhancers or sequences necessary for replication of a vector.

As described herein, hybridization analysis of Chinese Hamster somatic cell hybrids, each containing one human chromosome, indicated that bbp or genes closely related thereto, are located on chromosomes 2, 5 and X.

The complete Bak nucleotide and protein sequences are described in PCT Application No. PCT/US94/13930; Kiefer et al. (1995) *Nature* 374:736-739. As used herein, "bak" refers to the polynucleotide molecule, and derivatives thereof, described in the above-referenced patent application; "Bak" refers to the proteins encoded thereby and derivatives thereof.

Techniques for polynucleotide manipulation useful for the practice of the present invention are described in a variety of references, including but not limited to, *Molecular Cloning: A Laboratory Manual,* 2nd Ed., Vol. 1-3, eds. Sambrook et al. Cold Spring Harbor Laboratory Press (1989); and *Current Protocols in Molecular Biology,* eds. Ausubel et al., Greene Publishing and Wiley-Interscience: New York (1987) and periodic updates.

The bbp or bbpbd cDNA or genomic DNA can be incorporated into vectors for further manipulation. Furthermore, the invention concerns a recombinant DNA which is a recombinant vector comprising at least one of the above mentioned genes.

The recombinant vectors of the invention comprise an origin of replication or an autonomously replicating sequence, one or more dominant marker sequences and, optionally, expression control sequences, signal sequences and additional restriction sites.

Preferably, the recombinant vector of the invention comprises an above described nucleic acid insert operably linked to an expression control sequence, in particular those described hereinafter.

Vectors typically perform two functions in collaboration with compatible host cells. One function is to facilitate the cloning of the bbp gene or bbpbd, i.e., to produce useable quantities of the nucleic acid (cloning vectors). The other function is to provide for replication and expression of the gene constructs in a suitable host, either by maintenance as an extrachromosomal element or by integration into the host chromosome (expression vectors). A cloning vector comprises the DNAs as described above, an origin of replication or an autonomously replicating sequence, selectable marker sequences, and optionally, signal sequences and additional restriction sites. An expression vector additionally comprises expression control sequences essential for the transcription and translation of the bbp gene or bbpbd. Thus, an expression vector refers to a recombinant DNA construct, such as a plasmid, a phage, recombinant virus or other vector that, upon introduction into a suitable host cell, results in expression of the cloned DNA. Suitable expression vectors are well known in the art and include those that are replicable in eukaryotic and/or prokaryotic cells.

Most expression vectors are capable of replication in at least one class of organisms but can be transfected into another organism for expression. For example, a vector is cloned in *Escherichia coli* and then the same vector is transfected into yeast or mammalian cells even though it is not capable of replicating independently of the host cell chromosome. DNA can also be amplified by insertion into the host genome. However, the recovery, for example, of the genomic bbp gene is more complex than that of exogenously replicated vector because restriction enzyme digestion is required to excise the gene. DNA can be amplified by PCR and be directly transfected into the host cells without any replication component.

Advantageously, expression and cloning vectors contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g., ampicillin, neomycin, methotrexate or tetracycline, complement auxotrophic deficiencies, or supply critical nutrients not available from complex media.

Since the amplification of the vectors is conveniently done in E. coli, an E. coli genetic marker and an E. coli origin of replication are advantageously included. These can be obtained from E. coli plasmids, such as pBR322, BLUE-SCRIPT® vectors or a pUC plasmid or any other similar plasmid vector.

Suitable selectable markers for mammalian cells are those that enable the identification of cells competent to take up the bbp gene or bbpbd, such as dihydrofolate reductase (DHFR, methotrexate resistance), thymidine kinase, or genes conferring resistance to G418 or hygromycin. The mammalian cell transfectants are placed under selection pressure which only those transfectants are uniquely adapted to survive which have taken tip and are expressing the marker.

Expression and cloning vectors usually contain a promoter that is recognized by the host organism and is operably linked to the bbp gene or bbpbd. Suitable promoters can be inducible or constitutive. The promoters are operably linked to the gene of interest by removing the promoter from the source DNA by restriction enzyme digestion and inserting the isolated promoter sequence into the vector. Both the native promoter sequence and many heterologous promoters can be used to direct amplification and/or expression of a gene or fragment of interest. However, heterologous promoters are preferred, because they generally allow for greater transcription and higher yields of BBP or BBP Binding Domain as compared to native promoter.

Promoters suitable for use with prokaryotic hosts include, for example, the β-lactamase and lactose promoter systems, alkaline phosphatase, a tryptophan (trp) promoter system and hybrid promoters such as the tac promoter. Their nucleotide sequences have been published thereby enabling the skilled worker to ligate them to the gene of interest using linkers or adaptors to supply any required restriction sites. Promoters for use in bacterial systems will also generally contain a Shine-Dalgarno sequence operably linked to the gene.

Gene transcription from vectors in mammalian host cells can be controlled by promoters compatible with the host cell systems, e.g., promoters derived from the genomes of viruses. Suitable plasmids for expression of bbp or fragments of bak, such as bbpbd, in eukaryotic host cells, particularly mammalian cells, include, but are not limited to, cytomegalovirus (CMV) promoter-containing vectors, Rous Sarcoma Virus (RSV) promoter-containing vectors and SV40 promoter-containing vectors and MMTV LTR promoter-containing vectors. Depending on the nature of their regulation, promoters can be constitutive or regulatable by experimental conditions. Transcription of bbp or bak fragments according to the invention by higher eukaryotes can be increased by inserting an enhancer sequence into the vector. These promoters can also be cell type-specific, that is, inducible only in a particular cell type and often only during a specific period of time. The promoter can further be cell cycle specific, that is, induced or inducible only during a particular stage in the cell cycle.

The various DNA segments of the vector DNA are operably linked, i.e., they are contiguous and placed into a functional relationship to each other. Construction of vectors according to the invention employs conventional ligation techniques. Isolated plasmids or DNA fragments are cleaved, tailored and religated in the form desired to generate the plasmids required. If desired, analysis to confirm correct sequences in the constructed plasmids is performed in a manner known in the art. Suitable methods for constructing expression vectors, preparing in vitro transcripts, introducing DNA into host cells, and performing analyses for assessing bbp expression and function are known to those skilled in the art. Gene presence, amplification and/or expression can be measured in a sample directly, for example, by conventional Southern blotting, northern blotting to quantitate the transcription of mRNA, dot blotting (DNA or RNA analysis), in situ hybridization, using an appropriately labeled probe based on a sequence provided herein, binding assays, immunodetection and functional assays.

Nucleotides can also be expressed in non-human transgenic animals, particularly transgenic warm-blooded animals. Methods for producing transgenic animals, including mice, rats, rabbits, sheep and pigs, are known in the art and are disclosed, for example by Hammer et al. (1985) Nature 315: 680-683. An expression unit including a gene of interest together with appropriately positioned expression control sequences, is introduced into pronuclei of fertilized eggs. Introduction can be achieved, e.g., by microinjection. Integration of the injected DNA is detected, e.g., by blot analysis of DNA from suitable tissue samples. It is preferred that the introduced DNA be incorporated into the germ line of the animal so that it is passed to the animal's progeny.

Furthermore, a knock-out animal can be developed by introducing a mutation in the bbp or bbpbd sequence, thereby generating an animal which no longer expresses the functional bbp gene or bbpbd fragment. Such knock-out animals are useful, e.g., for studying the role of the BBP or BBP Binding Domain in apoptosis or other physiological functions.

More specifically, a knock-out animal can be developed (i.e., an animal that does not express the endogenous gene of interest), in which one introduces a mutated or wild-type gene. Methods for producing knock-out mice are known in the art. The knock-out animals are useful not only for studying the role of a given protein, as exemplified by published studies (see, e.g., Conquet et al. (1994) Nature 372:237-243; Aiba et al. (1994) Cell 79:365-375; and Masu et al. (1995) Cell 80:757-765), but also and, in particular, for providing a mammalian animal model with a suitable genetic background for introducing and expressing transgenes encoding the protein.

The nucleic acid sequences provided herein can be employed to identify DNAs encoding related polypeptides. A method for identifying such DNA comprises contacting DNA with a nucleic acid probe described above and identifying DNA(s) which hybridize to that probe. Bbp polynucleotides can also be used as probes or primers to detect a bbp gene or bbp RNA species to diagnose a phenotype characteristic of cells having elevated or reduced expression of BBP.

These methods are well known to those skilled in the art, and protocols can be found in a variety of sources, such as Ausubel (1993) *Current Protocols in Molecular Biology*, Green and Wiley, U.S.A., and periodic updates.

For an individual polypeptide related to BBP, the expression pattern in different tissues may vary. Thus, in order to isolate cDNA encoding a particular BBP-related polypeptide, it is advantageous to screen libraries prepared from different suitable tissues or cells. As a screening probe, there may be employed a DNA or RNA comprising substantially the entire coding region of bbp or a suitable oligonucleotide probe based on said DNA. A suitable oligonucleotide probe (for screening involving hybridization) is a single stranded DNA or RNA that has a sequence of nucleotides that includes at least 14 contiguous bases that are the same as (or complementary to) any 14 or more contiguous bases set forth in SEQ ID NO:6. The probe can be labeled with a suitable chemical moiety for ready detection. The nucleic acid sequences selected as probes should be of sufficient length and be sufficiently unambiguous so that false positive results are minimized.

Preferred regions from which to construct probes include 5' and/or 3' coding sequences, sequences predicted to encode ligand binding sites, and the like. For example, either the full-length cDNA clone disclosed herein or fragments thereof can be used as probes. Preferably, nucleic acid probes of the invention are labeled with suitable label means for ready detection upon hybridization. For example, a suitable label means is a radiolabel. The preferred method of labeling a DNA fragment is by incorporating $^{32}$P-labeled α-dATP with the Klenow fragment of DNA polymerase in a random priming reaction, as is well known in the art. Oligonucleotides are usually end-labeled with $^{32}$P-labeled γ-ATP and polynucleotide kinase. However, other methods (e.g., non-radioactive) can also be used to label the fragment or oligonucleotide, including, e.g., enzyme labeling and biotinylation.

After screening the library, e.g., with a portion of DNA including substantially the entire bbp gene or a suitable oligonucleotide based on a portion of said DNA, positive clones are identified by detecting a hybridization signal; the identified clones are characterized by restriction enzyme mapping and/or DNA sequence analysis, and then examined, e.g., by comparison with the sequences set forth herein, to ascertain whether they include a full length bbp gene (i.e., if they include translation initiation and termination codons). If the selected clones are incomplete, they can be used to rescreen the same or a different library to obtain overlapping clones. If the library is genomic, then the overlapping clones can include exons and introns. If the library is a cDNA library, then the overlapping clones will include an open reading frame. In both instances, complete clones can be identified by comparison with the DNAs and deduced amino acid sequences provided herein.

Furthermore, in order to detect any abnormality of an endogenous bbp or bak, genetic screening can be carried out using a nucleotide sequence of the invention as hybridization probes. Genetic defects due to a mutation in a bbp gene or bbpbd sequence can lead to aberrant expression of BBP or Bak, or to expression of an aberrant BBP or Bak, which may not associate properly with a other proteins in the cell. As a result, a genetic defect in a bbp or bak gene could result in a pathology characterized by increased or decreased apoptosis. Oligonucleotide probes comprising a nucleotide sequence of the bbp or bbpbd polynucleotides disclosed herein can be used to identify cells having a mutation in a bbp or bak gene using well known hybridization methods. In order to provide the specificity necessary to identify, for example, a point mutation in a bbp gene, one skilled in the art would know that an oligonucleotide probe should be at least about fourteen to sixteen nucleotides in length. In addition, the probe should incorporate a detectable moiety such as a radiolabel, a fluorochrome or a detectable binding agent such as biotin. Various detectable moieties and methods of incorporating the moiety into an oligonucleotide probe are well known in the art and are commercially available.

Also, based on the nucleic acid sequences provided herein antisense-type or ribozyme therapeutic agents can be designed and are included in the scope of the invention. For example, oligoribonucleotides, including antisense RNA and DNA molecules and ribozymes can function to inhibit translation of one or more components of a protein complex. S. T. Crooke and B. Lebleu, eds. *Antisense Research and Applications* (1993) CRC Press. Anti-sense RNA and DNA molecules act to directly block the translation of mRNA by binding to targeted mRNA and preventing protein translation. With respect to antisense DNA, oligodeoxyribonucleotides derived from the translation initiation site, e.g., between −10 and +10 regions of the relevant nucleotide sequence, are preferred.

Ribozymes are enzymatic RNA molecules capable of catalyzing the specific cleavage of RNA. The mechanism of ribozyme action involves sequence specific interaction of the ribozyme molecule to complementary target RNA, followed by an endonucleolytic cleavage. Within the scope of the invention are engineered hammerhead or other motif ribozyme molecules that specifically and efficiently catalyze endonucleolytic cleavage of RNA sequences encoding protein complex components.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site can be evaluated for predicted structural features, such as secondary structure, that may render the oligonucleotide sequence unsuitable. The suitability of candidate targets can also be evaluated by testing their accessibility to hybridization with complementary oligonucleotides, using ribonuclease protection assays. See, Draper PCT WO 93/23569.

Both anti-sense RNA and DNA molecules and ribozymes of the invention can be prepared by any method known in the art for the synthesis of RNA molecules. See, Draper, id. These include techniques for chemically synthesizing oligodeoxyribonucleotides well known in the art including, but not limited to, solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules can be introduced as a means of increasing intracellular stability and half-life. Possible modifications include, but are not limited to, the addition of flanking sequences or ribo- or deoxyribonucleotides to the 5' and/or 3' O-methyl rather than phosphodiesterase linkages within the oligodeoxyribonucleotide backbone.

It is envisaged that the nucleic acid of the invention can be readily modified by nucleotide substitution, nucleotide deletion, nucleotide insertion or inversion of a nucleotide stretch, and any combination thereof. Such modified sequences can be used to produce a mutant BBP which differs from those found in nature. Mutagenesis can be predetermined (site-specific) or random. A mutation which is not a silent mutation should not place sequences out of reading frames and preferably will not create complementary regions that could hybridize to produce secondary mRNA structures such as loops or hairpins.

Given the guidance of the present invention, the nucleic acids of the invention are obtainable according to the methods well known in the art. The present invention further relates to a process for the preparation of such nucleic acids.

For example, a DNA of the invention is obtainable by chemical synthesis, by recombinant DNA technology or by PCR. Preparation by recombinant DNA technology can involve screening a suitable cDNA or genomic library. A suitable method for preparing a DNA or of the invention can, e.g., comprise the synthesis of a number of oligonucleotides, their amplification by PCR methods, and their splicing to give the desired DNA sequence. Suitable libraries are commercially available or can be prepared from individual tissues or cell lines.

Suitable antibodies for use herein are generated by using BBP or fragments of BBP as an antigen. Antibodies to a BBP Binding Domain or Bak are also suitable for use herein. Methods of detecting proteins using antibodies and of generating antibodies using proteins or synthetic peptides are known in the art and are not described in detail herein.

The present invention further encompasses antibodies or antigen binding fragments that recognize BBP or BBP Binding Domain, or fragments thereof. Such antibodies can be useful e.g. for immunoassays including immunohistochemistry, in the detection of a substances that bind to BBP or BBP Binding Domain, or, alternatively, for use in purification or identification of BBP or BBP Binding Domain or antigenically related polypeptides, or for diagnostic or therapeutic purposes. For example, an antibody can be used to detect the presence of a BBP in a biological sample. The cells can either be lysed or permeabilized to the antibody, both are acceptable methods of exposing the contents of the cells to antibodies, using methods known in the art.

Antibodies which can be used as therapeutic or diagnostic agents include polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above. Antibodies can be of any immunoglobulin class including IgG, IgM, IgE, IgA, IgD and any subclass thereof.

Polyclonal antibodies are heterogeneous populations of antibody molecules derived from the sera of animals immunized with an antigen, such as a protein-protein complex, or individual components. For the production of polyclonal antibodies, various host animals can be immunized by injection with the antigen such as rabbits, mice, and rats. Various adjuvants can be used to increase the immunological response, depending on the host species, such as Freund's (complete and incomplete), mineral gels (e.g., lysolecithin, pluronic polyols, polyanions, peptides, oil emulsions, keyhole limpet hemocyanin, dinitrophenol), and potentially useful human adjuvants such as BCG (bacille Calmette-Guerin) and *Corynebacterium parvum.*

A monoclonal antibody, which is a substantially homogeneous population of antibodies to a particular antigen, can be obtained by techniques providing for the production of antibody molecules by continuous cell lines in culture. Examples of such techniques include the hybridoma technique described by Kohler and Milstein (1975) *Nature* 256:495497, the human B-cell hybridoma technique (Olsson et al. *J. Immunol. Methods* 61:17-32; and Cole et al. (1984) *Mol. Cell. Biochem.* 62:109-120), and the EBV-hybridoma technique (Roder et al. (1986) *Methods Enzymol.* 121:140-167). The hybridoma producing the mAb can be cultivated in vitro or in vivo.

In addition, techniques developed for the production of "chimeric antibodies" (Morrison et al. (1984) *Proc. Natl. Acad. Sci. USA* 81:6851-6855; Neuberger et al. (1984) *Nature* 312:604-608; and Takeda et al. (1985) *Nature* 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird (1988) *Science* 242:423-426; Huston et al. (1988) *Proc. Natl. Acad. Sci. USA* 85:5879-5883; and Ward et al. (1989) *Nature* 334: 544-546) can be adapted to produce antigen-specific single chain antibodies. Single chain antibodies are formed by linking the heavy and light chain fragment of the Fv region via an amino acid bridge, resulting in a single chain polypeptide.

Antibody fragments containing specific binding sites of a complex can be generated by known techniques. For example, such fragments include the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries can be constructed (Huse et al. (1989) *Science* 246:1275-1281) to allow rapid and easy identification of monoclonal Fab fragments with the desired specificity to BBP or BBP Binding Domain.

The invention further provides methods for detecting agents that can modulate the interaction between a BBP and a Bak protein or BBP Binding Domain of the Bak protein. "Modulate" in this sense means to alter the ability of a BBP to associate with a Bak protein. Thus, modulation includes enhancement of the association between a BBP and a Bak protein, as well as dissociation of a bound complex formed by the association of a BBP and a Bak protein. Methods for detecting an agent that can modulate the interaction between a Bak and a BBP are known in the art and include, but are not limited to, yeast two-hybrid screening, phage display and assays such as the one described in Example 6.

As used herein, the term "agent" means a chemical or biological molecule such as a simple or complex organic molecule, a peptide, a protein or an oligonucleotide. An "effective agent" is an agent that, in fact, alters an interaction of proteins involved in apoptosis. An effective agent is therefore also a potential therapeutic agent.

The screening assay described herein is particularly useful in that it can be automated, which allows for high through-put screening of randomly designed agents to identify useful drugs, which can alter the ability of a BBP and a Bak protein to associate. For example, a drug can alter the ability of a BBP and a Bak protein to associate by decreasing or inhibiting the binding affinity of a BBP and a Bak protein. Such a drug can be useful where it is desirable to increase the concentration of unbound Bak in a cell, for example, so that free Bak is available to induce apoptosis. Alternatively, a drug can be useful for increasing the affinity of binding of a BBP and a Bak protein.

The drug screening assay can utilize BBP or a BBP fusion protein such as a BBP-glutathione-S-transferase (gst). The BBP or BBP fusion protein is characterized, in part, by having an affinity for a solid substrate as well as having an affinity for a Bak protein. For example, when BBP is used in the assay, the solid substrate can contain a covalently attached anti-BBP antibody. Alternatively, a BBP-gst fusion protein can be used in the assay. Where such a fusion protein is used in the assay, the solid substrate can contain covalently attached glutathione, which is bound by the gst component of the BBP-gst fusion protein.

The drug screening assay can be performed by allowing the BBP or BBP-fusion protein to bind to the solid support, then adding a Bak protein and a drug to be tested. Control reactions will not contain the drug. Following incubation of the reaction mixture under conditions known to be favorable for the association, for example, of BBP and Bak in the absence of a drug, the amount of Bak specifically bound to BBP in the presence of a drug can be determined. For ease of detecting binding, the Bak protein can be labeled with a detectable moiety, such as a radionuclide or a fluorescent label, using methods well known in the art. By comparing the amount of specific binding of BBP and Bak in the presence of a drug as compared to the control level of binding, a drug that increases or decreases the binding of a BBP and a Bak protein can be identified. Thus, the drug screening assay provides a rapid and simple method for selecting drugs having a desirable effect on the association of a BBP and a Bak protein.

A transcription activation assay such as the yeast two-hybrid system allows for the identification and manipulation of protein-protein interactions. Fields and Song (1989) *Nature* 340:245-246. The conceptual basis for a transcription activation assay is predicated on the modular nature of transcription factors, which consist of functionally separable DNA-binding and trans-activation domains. When expressed as separate proteins, these two domains fail to mediate gene transcription. However, the ability to activate transcription can be restored if the DNA-binding domain and the trans-activation domain are bridged together through a protein-protein interaction. These domains can be bridged, for example, by expressing the DNA-binding domain and trans-activation domain as fusion proteins (hybrids), where the proteins that are appended to these domains can interact with each other. The protein-protein interaction of the hybrids can bring the DNA-binding and trans-activation domains together to create a transcriptionally competent complex.

A transcription activation assay such as the yeast two hybrid system can also be useful as a screening assay to identify effective agents that alter interactions between a Bak and a BBP. A transcription activation assay can be used to screen a panel of agents to identify an effective agent, which can be useful for increasing or decreasing apoptosis in a cell.

An effective agent can be identified by detecting an altered level of transcription of a reporter gene. For example, the level of transcription of a reporter gene due to the bridging of a DNA-binding domain and trans-activation domain by a BBP and a Bak protein can be determined in the absence and in the presence of an agent. An effective agent that increases the interaction between a Bak protein and a BBP can be identified by an increased level of transcription of the reporter gene as compared to the control level of transcription in the absence of the agent.

An agent that effectively increases the interaction of Bak and BBP, as detected by increased transcription of the reporter gene in a two-hybrid assay, can be used to alter the level of apoptosis in a cell. An effective agent that decreases the interaction of Bak and BBP also can be identified, in this case by detecting a decreased level of transcription of a reporter gene as compared to the level of transcription in the absence of the agent. Effective agents that result in decreased levels of apoptosis can be particularly useful as a medicament for treating a patient suffering from a disease characterized by a high level of apoptosis such as a neurodegenerative disease. Effective agents that result in increased levels of apoptosis can be useful, for example, to increase the level of apoptosis of a cancer cell, which is characterized by having a decreased level of apoptosis as compared to its normal cell counterpart. Thus, effective agents identified using the methods described herein are particularly useful as medicaments to increase or decrease the level of apoptosis in a cell in a subject.

In some cases, an agent may not be able to cross the yeast cell wall and, therefore, cannot enter the yeast cell to alter an interaction among members of the Bak protein family. The use of yeast spheroplasts, which are yeast cells that lack a cell wall, can circumvent this problem (Smith and Corcoran, In *Current Protocols in Molecular Biology* (ed. Ausubel et al.; Green Publ., NY 1989)). In addition, a potentially effective agent, upon entering a cell, may require "activation" by a cellular mechanism, which may not be present in yeast. Activation of an agent can include, for example, metabolic processing of the agent or a modification such as phosphorylation of the agent, which can be necessary to convert the agent into an effective agent. In this case, a mammalian cell line can be used to screen a panel of agents. A transcription assay such as the yeast two-hybrid system described in Example 1 can be adapted for use in mammalian cells using well known methods (Fearon et al. (1992) *Proc. Natl. Acad. Sci. USA* 89:7958-7962; see, also, Sambrook et al., *Molecular Cloning: A Laboratory Manual* (Cold Spring Harbor Laboratory Press 1989), and Ausubel et al., *Current Protocols in Molecular Biology* (Green Publ., NY 1989).

It may be advantageous to employ a peptide analog of BBP or Bak, or a portion thereof, as a pharmaceutical agent or as a commercial research reagent. For example, a peptide analog of BBP having high affinity for binding Bak can be used as a competitive inhibitor of BBP:Bak complex formation by competing with native BBP for binding to Bak.

In addition to polypeptides consisting only of naturally-occurring amino acids, peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" and are usually developed with the aid of computerized molecular modeling. Eichler et al. (1995) *Med. Res. Rev.* 15:481-496; Moore et al. (1995) *Adv. Pharmacol.* 33:1-41; Moore (1994) *Trends Pharmacol. Sci.* 15:124-129; Saragovi et al. (1992) *Biotechnol.* 10:773-778. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biochemical property or pharmacological activity), such as Bak, but have one or more peptide linkages optionally replaced by a linkage such as: —$CH_2NH$—, —$CH_2S$—, —$CH_2$—$CH_2$—, —CH=CH— (cis and trans), —$COCH_2$—, —CH(OH)$CH_2$—, and —$CH_2SO$—, by methods known in the art. See, for example, Spatola (1983) *Chemistry and Biochemistry of Amino Acids, Peptides, and Proteins* B. Weinstein eds. Marcel Dekker, New York.

Such peptide mimetics can have significant advantages over polypeptide embodiments, including, for example, more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecule(s) (e.g., are not contact points in Bak:BBP complexes) to which the peptidomimetic binds to produce the therapeutic effect. Derivitization (e.g., labeling) of peptidomimetics should not substantially interfere with the desired biological or pharmacological activity of the peptidomimetic.

The invention also provides methods for identifying polypeptide sequences which bind to a BBP polypeptide. For example, a yeast two-hybrid screening system can be used for identifying polypeptide sequences that bind to BBP. Yeast two-hybrid systems wherein one GAL4 fusion protein comprises a BBP polypeptide sequence, typically a full-length or near full-length BBP sequence, and the other GAL4 fusion protein comprises a cDNA library member can be used to identify cDNAs encoding proteins which interact with the BBP polypeptide, can be screened according to the general method of Chien et al. (1991) *Proc. Natl. Acad. Sci. USA* 88:9578-9582. Other methods for detecting BBP-binding proteins are known in the art and include, but are not limited to screening a phage display library with a BBP. U.S. Pat. No. 5,223,409.

As used herein, the terms "suitable conditions" or "appropriate conditions" refer to temperature, pH, ionic strength, viscosity and biochemical parameters which are compatible with physiological protein-protein interactions. Suitable in vitro or in vivo reaction conditions for protein-protein interactions are generally physiological conditions. In general, in vitro physiological conditions comprise 50-200 mM NaCl or KCl, pH 6.5-8.5, 20° C.-45° C. and 0.001-10 mM divalent cation (e.g., $Mg^{++}$, $Ca^{++}$); preferably about 150 mM NaCl or KCl, pH 7.2-7.6, 5 mM divalent cation, and often include 0.01-1.0% nonspecific protein (e.g., bovine serum albumin). Particular aqueous conditions can be selected by the practitioner according to conventional methods. Addition of other components is optional and the additional components and reaction conditions can vary according to a particular need.

In another embodiment, diagnostic methods are provided to detect the expression of BBP either at the protein level or the mRNA level. Any antibody that specifically recognizes BBP is suitable for use in BBP diagnostics. Abnormal levels of BBP may be found in the tissues of patients with diseases associated with inappropriate apoptosis; diagnostic methods are therefore useful for detecting and monitoring biological conditions associated with such apoptosis defects. Detection methods are also useful for monitoring the success of BBP-related therapies.

BBP protein expression can also be monitored by measuring the level of bbp mRNA. Any method for detecting specific mRNA species is suitable for use in this method. This is easily accomplished using the polymerase chain reaction (PCR). Alternatively, Northern blots can be utilized to detect bbp mRNA or bak mRNA by using probes specific to bbp or bbpbd. Methods of utilizing PCR and Northern blots are known in the art and are not described in detail herein.

The invention further provides methods for modulating the activity of Bak or a Bak-related protein in a cell by introducing into the cell a nucleotide sequence encoding BBP or an antisense nucleotide sequence, which is complementary to a region of a gene encoding BBP and can hybridize to the gene or to an mRNA transcribed from the gene. As used herein, the term "modulate" means the level of a BBP expressed in a cell can be increased or decreased. Thus, the compounds described herein can be used as medicaments for the treatment of a pathology caused by an altered level of apoptosis.

The level of a gene product such as BBP or BBP Binding Domain can be increased in a cell using recombinant expression vectors and gene transfer technology to express a nucleic acid encoding BBP or BBP Binding Domain or an active fragment of BBP or BBP Binding Domain. Various expression vectors and methods for introducing such vectors into a cell are well known in the art and are described, for example, in Sambrook et al. (1989). Viral vectors that are compatible with a targeted cell are particularly useful for introducing a nucleic acid encoding BBP or BBP Binding Domain into a cell. For example, recombinant adenoviruses having general or tissue-specific promoters can be used to deliver expression constructs into a variety of types of tissues and cells, including non-mitotic cells, and to drive the desired cDNA expression in the target cells. Recombinant adeno-associated viruses also are useful and have the added advantage that the recombinant virus can stably integrate into the chromatin of even quiescent non-proliferating cells such as neurons of the central and peripheral nervous systems. Lebkowski et al. (1988) *Mol. Cell. Biol.* 8:3988-3996.

Suitable indications for modulating endogenous levels of BBP or BBP Binding Domain are any in which BBP or BBP Binding Domain-mediated apoptosis is involved. These include, but are not limited to, various types of malignancies and other disorders resulting in uncontrolled cell growth such as eczema, or deficiencies in normal programmed cell death such as malignancies, including, but not limited to, B cell lymphomas.

Methods of treatment with BBP also include modulating cellular expression of BBP by increasing or decreasing levels of bbp mRNA or protein. Suitable methods of increasing cellular expression of BBP or BBP Binding Domain include, but are not limited to, increasing endogenous expression and transfecting the cells with vectors encoding bbp or bbpbd, respectively.

For purposes of gene therapy, the level of BBP or a BBP Binding Domain can be increased in a cell using recombinant expression vectors and gene transfer technology to express bbp or bbpbd or a portion thereof. Viral vectors that are compatible with a targeted cell are particularly useful for introducing a bbp or bbpbd gene into a cell. For example, recombinant adenoviruses having general or tissue-specific promoters can be used to deliver bbp constructs into a variety of types of tissues and cells. Retroviral vectors are often used for in vivo targeting and therapy procedures. Retroviral vectors can be constructed either to function as infectious particles or to undergo only a single initial round of infection. Methods for constructing and using viral vectors are known in the art and are reviewed, for example, in Miller and Rosman (1989) *Biotechniques* 7:980-982.

The invention encompasses ex vivo transfection with bbp or bbpbd, in which cells removed from animals including man are transfected with vectors encoding BBP or BBP Binding Domain and reintroduced into animals. Suitable transfected cells include individual cells or cells contained within whole tissues. In addition, ex vivo transfection can include the transfection of cells derived from an animal other than the animal or human subject into which the cells are ultimately introduced. Such grafts include, but are not limited to, allografts, xenografts, and fetal tissue transplantation. Essentially any cell or tissue type can be treated in this manner. Suitable cells include, but are not limited to, cardiomyocytes and lymphocytes. Transfection methods include, but are not limited to calcium phosphate precipitation and DEAE-dextran or lipofectin facilitated transfection; these methods are well known in the art and are described in, for example, Sambrook et al. (1989).

Further, the invention encompasses cells transfected in vivo by vectors containing bbp or bbpbd cDNA. Suitable methods of in vivo transfection are known in the art and include, but are not limited to, that described by Zhu et al. (1993) Science 261:209-211. Receptor-mediated DNA delivery approaches also can be used to deliver BBP or BBP Binding Domain expression plasmids into cells in a tissue-specific fashion using a tissue-specific ligand or antibody non-covalently complexed with DNA via bridging molecules. Curiel et al. (1992) Hum. Gene Ther. 3:147-154; and Wu and Wu (1987) J. Biol. Chem. 262:4429-4432. Direct injection of DNA or DNA encapsulated in cationic liposomes also can be used for stable gene transfer to non-dividing and dividing cells in vivo, Ulmer et al. (1993) Science 259:1745-1749. In addition, DNA can be transferred into a variety of cell types using the particle bombardment method. Heiser (1994) Anal. Biochem. 217:185-196; Yang et al. (1990) Proc. Natl. Acad. Sci. USA 87:9568-9572. In vivo transfection by bbp may be particularly useful as a prophylactic treatment for patients suffering from atherosclerosis. Modulation of the levels of BBP or BBP Binding Domain could serve as a prophylaxis for the apoptosis-associated reperfusion damage that results from cerebral and myocardial infarctions. In these patients with a high risk of stroke and heart attack, the apoptosis and reperfusion damage associated with arterial obstruction could be prevented or at least mitigated.

Infarctions are caused by a sudden insufficiency of arterial or venous blood supply due to emboli, thrombi, or pressure that produces a macroscopic area of necrosis; the heart, brain, spleen, kidney, intestine, lung and testes are likely to be affected. Apoptosis occurs to tissues surrounding the infarct upon reperfusion of blood to the area; thus, modulation of BBP or BBP Binding Domain levels, achieved by a biological modifier-induced change in endogenous production or by in vivo transfection, could be effective at reducing the severity of damage caused by heart attacks and stroke.

In addition, increasing endogenous expression of BBP can be accomplished by exposing the cells to biological modifiers that directly or indirectly increase levels of BBP either by increasing expression or by decreasing degradation of bbp mRNA. Suitable biological modifiers include, but are not limited to, molecules and other cells. Suitable molecules include, but are not limited to, drugs, cytokines, small molecules, hormones, combinations of interleukins, lectins and other stimulating agents e.g. PMA, LPS, bispecific antibodies and other agents which modify cellular functions or protein expression. Cells are exposed to such biological modifiers at physiologically effective concentrations, and the expression of BBP is measured relative to a control not exposed to the biological modifiers. Those biological modifiers which increase expression of BBP relative to the control are selected for further study.

The invention further encompasses a method of decreasing endogenous levels of BBP or BBP Binding Domain. The methods of decreasing endogenous levels of BBP or BBP Binding Domain include, but are not limited to, antisense nucleotide therapy and down-regulation of expression by biological modifiers. Antisense therapy is known in the art and its application will be apparent to one of skill in the art. Homologous recombinant gene knock-out methods can also be used to decrease the level of BBP or BBP Binding Domain in a cell. Capecchi (1990) Nature 344:105.

The following examples are provided to illustrate but not limit the present invention. Unless otherwise specified, all cloning techniques were essentially as described by Sambrook et al. (1989) and all reagents were used according to the manufacturer's instructions.

Example 1

Identification and Cloning of BBP cDNA

BBP cDNA was discovered in human heart using the yeast two hybrid system. The requirement of the DNA binding and activation domains of the yeast transcriptional activator GAL4 for the induction of the GAL1 promoter and the ability of those functions to operate even when on separate fusion proteins provides the basis for the assay and allows detection of associating proteins. The strategy used to detect proteins with binding affinity for Bak is shown in FIG. 1.

The GAL4-Bak fusion protein consisted of amino acids 1-147 of GAL4, a region that directs binding of GAL4 to the upstream activator sequence of the GAL1 promoter. The Bak protein, or BakΔ2-TM, whose amino acid sequences are shown in FIG. 2 and FIG. 3, respectively, served as the "bait". The lacZ gene under the control of the GAL1 promoter constituted the first reporter system. The second reporter system consisted of the histidine reporter gene similarly under transcriptional control of the GAL1 promoter. Yeast possessing a dual reporter system responsive to transcriptional activation through the GAL1 promoter were transformed with a plasmid expressing a GAL4-Bak fusion protein. A cDNA library from human heart mRNA was purchased from Clontech and cloned into the vector pGAD10 such that members of the library would be constitutively expressed as a fusion protein with amino acids 768-881 of GAL4, a region containing the transcriptional activation domain. Yeast cells containing library proteins that interact with the bait protein, Bak or BakΔ2-TM, turn blue when grown on medium containing XGal, which yields a chromogenic product when acted on by β-galactosidase. Yeast cells were transformed by the lithium acetate method. Ito et al. (1983) J. Bacteriol. 153:163-168.

Full length bak or truncated balΔ2-TM (aa71-187) constructs were amplified by PCR from cDNA as EcoRI fragments and cloned as in-frame fusions to the GAL4 DNA binding domain into the vectors pGBT9 and pAS2-1, respectively (Clontech, Palo Alto, Calif.). A human heart cDNA library of $3 \times 10^6$ independent clones in pGAD10 (Clontech) was amplified and cotransformed into yeast strain CG1945 (Clontech) with Bak bait plasmids. Histidine positive transformants were assayed for β-galactosidase activity by the filter method. Plasmid DNA was isolated from all His+/X-Gal+ clones by the rapid technique recommended by Clontech or by spheroplasting and subsequent alkaline lysis. This DNA was amplified by PCR to determine insert size. pGAD10 clones were isolated by transforming E. coli strain HB101 and selecting on M9 Leucine-Ampicillin plates. Plasmids were sorted by restriction enzyme digest and Southern blot and then sequenced.

Twenty-six clones activated both the β-galactosidase and histidine reporter genes. Sixteen clones encoded the same protein, which was termed BBP. DNA sequence analysis of BBP cDNA, shown in FIG. 4, revealed an open reading frame encoding a 151 amino acid protein, with a predicted relative mass of 16 kD. TopPredII, a program for predicting membrane protein structure, indicated that BBP was a three trans-membrane protein with hydrophilic N-terminal 42 amino acid region and a 58 amino acid loop region, both located on the cytoplasmic side of the membrane.

Example 2

Northern Blot Analysis of cDNA Clones

Northern blot analysis was performed according to the method described by Lehrach et al. (1977) *Biochem.* 16:4743-4751 and Thomas (1980) *Proc. Natl. Acad. Sci. USA* 77:5201-5205. In addition, a human multiple tissue Northern blot was purchased from Clontech. The coding regions of BBP cDNA was labeled by the random priming method described by Feinberg and Vogelstein (1984) *Anal. Biochem.* 137:266-267. Hybridization and washing conditions were performed according to standard methods.

Figure 5:
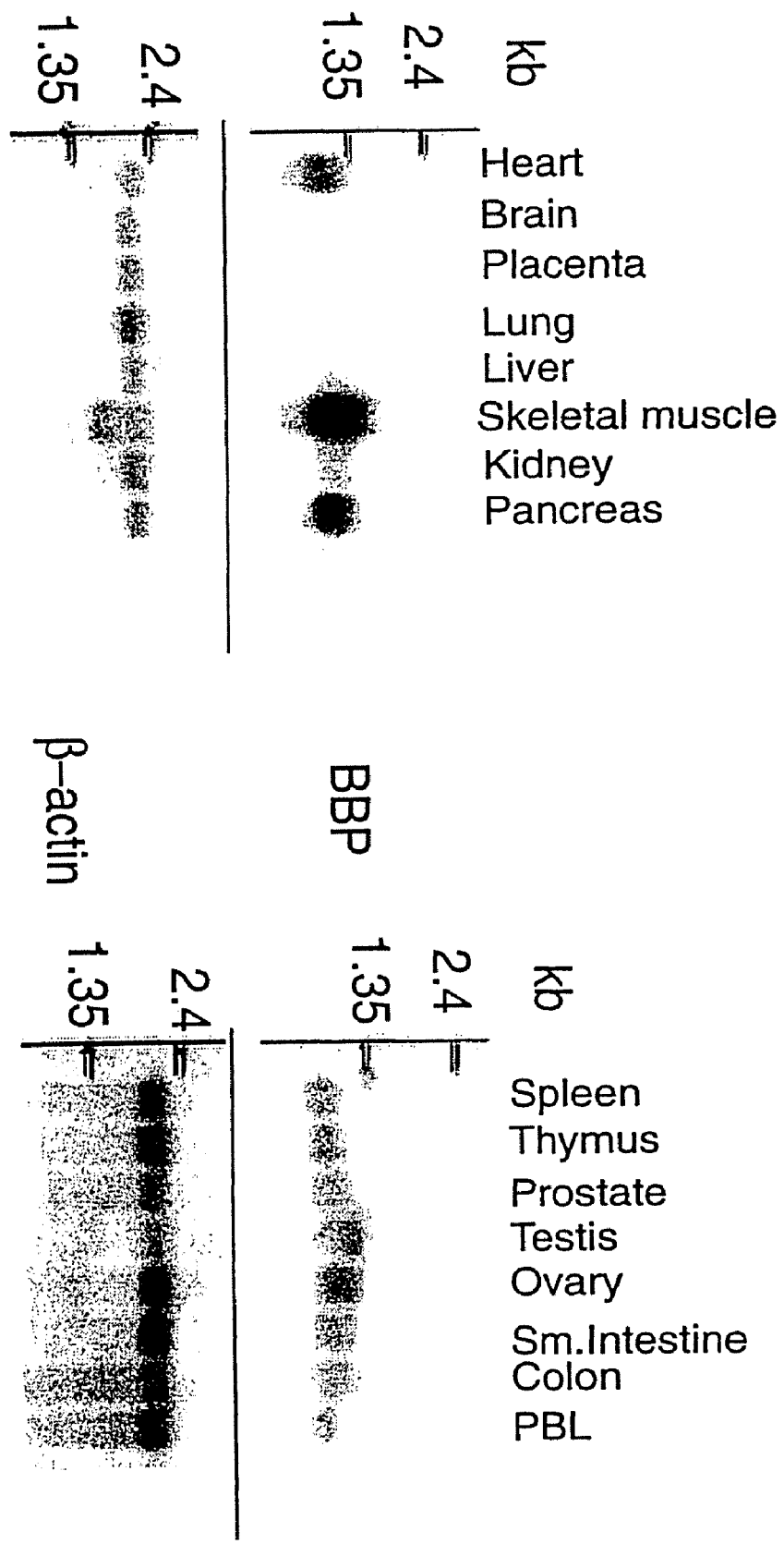
FIG. 5 depicts the results of a Northern blot analysis of multiple tissues with probes specific for BBP.

The results, presented in FIG. 5, indicate that BBP shows a wide tissue distribution among the organs tested (heart, brain, placenta, lung, liver, skeletal muscle, kidney and pancreas), with high levels of a 1.2 kb mRNA found in heart, skeletal muscle and pancreas.

Example 3

BBP Interacts with Itself and with BAK

Figure 6:
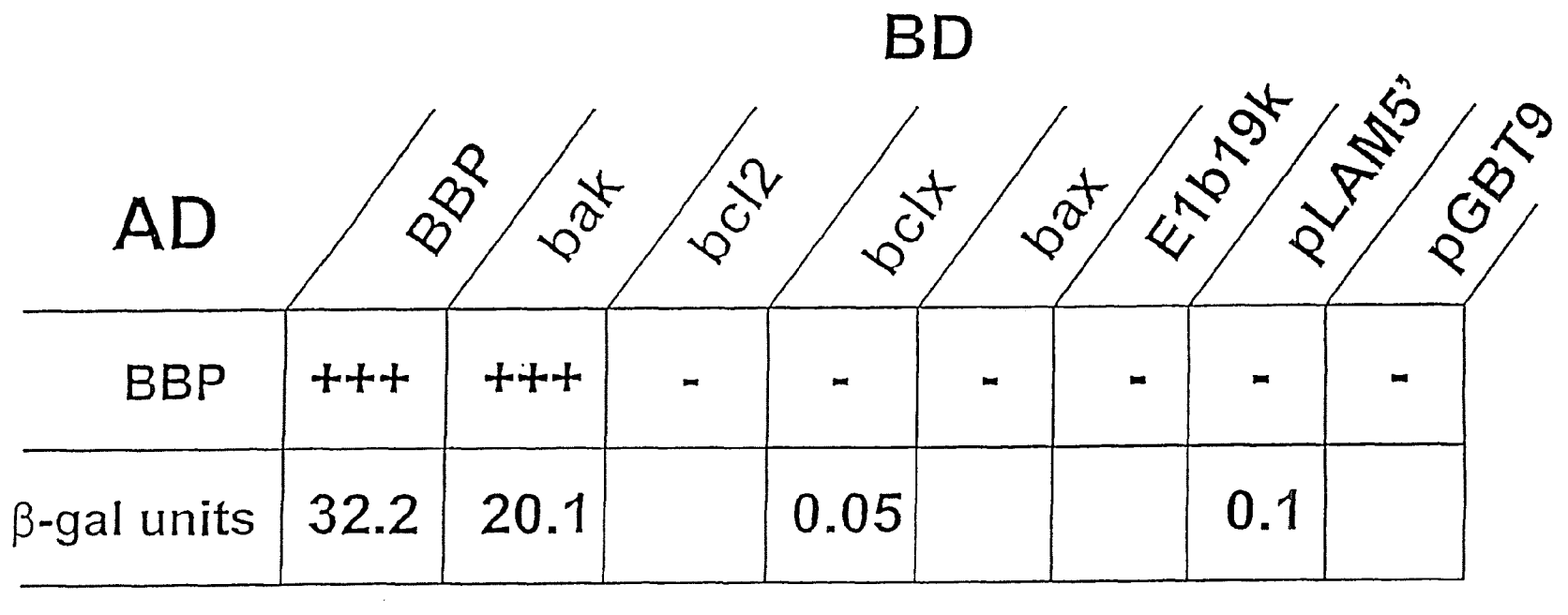

Using the yeast two hybrid system described above, the interactions between BBP and members of the bcl2 family of apoptosis modulators, as well as with BBP itself, were analyzed. BBP was expressed as a fusion protein with the activation domain (AD) of GAL4. Genes encoding BBP, Bak, Bcl2, Bclx, Bax and E1B19k proteins were inserted into expression vectors containing the coding sequence for the binding domain of GAL4 such that these proteins would be expressed as fusion proteins with the binding domain (BD) of GAL4. Results, summarized in FIG. 6, indicated that BBP associates with itself and with Bak, but not with the other members of the bcl2 family that were tested.

Example 4

Copy Number and Chromosomal Location of bbp

Southern blot analysis was used to determine gene copy number and size of the bbp gene(s). Restriction analysis of human genomic DNA with several enzymes, including BamHI, EcoRI and HindIII, revealed multiple bands hybridizing to the bbp cDNA. EcoRI generated eight bands ranging in size from 1.5 to 15 kilobase pairs (kb). Similar patterns were seen with BamHI and HindIII. To investigate the number and distribution of bbp genes, a Somatic Cell Hybrid Panel of human chromosomes was obtained from Coriell Cell Repositories (Camden, N.J.). Each mouse or Chinese Hamster somatic cell hybrid contains one human chromosome. Genomic DNA from these hybrids was digested with EcoRI along with human, mouse and Chinese Hamster genomic DNA controls. Under stringent hybridization conditions (0.1×SSC, 0.1% SDS, 65° C.) with the bbp cDNA, genes were found to reside on human chromosomes 2, 5 and X and align with eight bands seen with total human genomic DNA. Thus, there are at least three gene members in the BBP family.

Example 5

Examination of Bak Interactions with BBP

To delineate the regions of Bak and BBP that mediate the association of these two proteins, two series of experiments were conducted in which portions of BBP fused to glutathione-S-transferase (gst) were allowed to interact with Bak or derivatives thereof.

In the first series of experiments, gst fusion proteins were made that contained the two hydrophilic regions of BBP, full-length E1B19K or full-length BHRF-1. The hydrophilic regions of BBP are the N-terminal 42 amino acid portion and an internal loop of BBP consisting of amino acids 86 through 133, and are referred to as BBP-Loop1 (BBP-L1) and BBP-Loop2 (BBP-L2), respectively. DNA sequences encoding the hydrophilic regions were amplified by polymerase chain reaction (PCR) and subcloned into pGEX-5X (Pharmacia) in-frame with gst.

Figure 7:
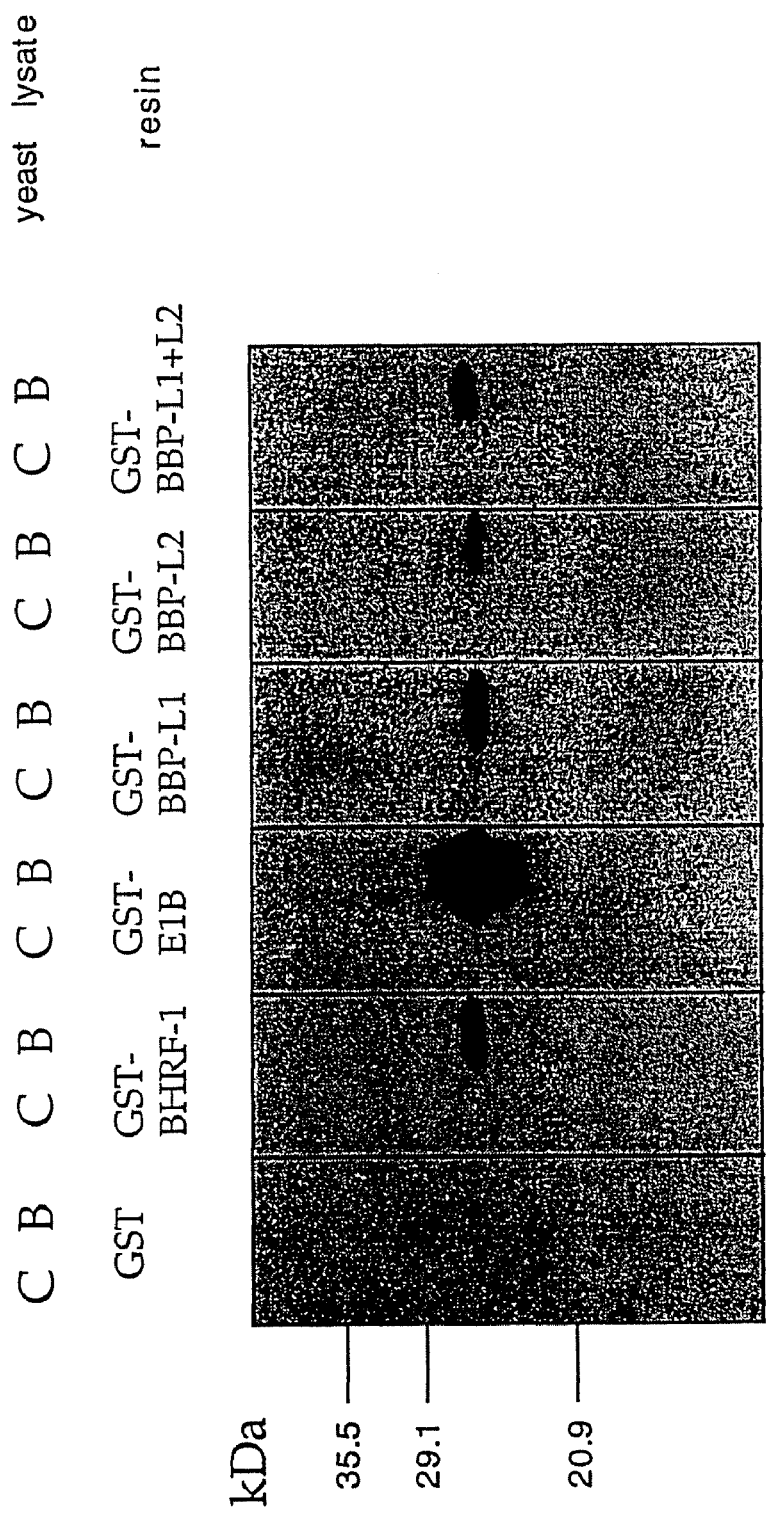
FIG. 7 shows the results of Western blot analysis of the interactions between BBP, BBP derivatives, BHRF-1, E1B19K and Bak.

Gst fusion proteins containing BBP-L1, BBP-L2, E1B19K or BHRF-1 were immobilized on a glutathione-Sepharose column. Yeast lysates expressing Bak or control vector were passed over the column, washed and Bak binding was assessed by Western blot analysis. As had been previously shown, Bak interacted with BHRF-1 and E1B19K. Bak was also shown to interact with the N-terminal 42 amino acid region of BBP and with the internal loop (FIG. 7).

To define further the interaction between Bak and BBP, a peptide consisting of amino acids 1-50 of Bak was used in place of full-length Bak and binding to immobilized BBP-L1 or BBP-L2 was assessed. The synthetic peptide of the first 50 residues of Bak (Bak 1-50) was supplied by Pharmingen. This peptide is soluble in 1× phosphate-buffered saline (PBS).

For each of the three glutathione SEPHAROSE®/gst fusion protein complexes (representing BBP-L1, BBP-L2 and a control), 100 µg of Bak 1-50 (in 1 ml of PBS/0.1% TRITON® X-100, a nonionic surfactant) was added to 50 µL of resin in an Eppendorf tube and left overnight at 4° C. Duplicate samples were prepared lacking the peptide in the PBS/0.1% TRITON® X-100 (nonionic surfactant) buffer. The following day, the resins were washed 5 times with the PBS/0.1% TRITON® X-100 (nonionic surfactant) buffer and then the resins boiled in 50 µL 1× sodium dodecyl sulfate-polyacrylamide gel electrophoresis (SDS PAGE) sample loading buffer. A western was performed to assess the protein-protein interactions. The results, shown in FIG. 8A, demonstrate that a region in the first 50 amino acids of Bak is capable of interacting with both BBP-L1 and BBP-L2.

In a second series of experiments, an N-terminal deletion of Bak was made and analyzed in a similar manner as above for binding to the hydrophilic regions of BBP. The N-terminal deletion mutant of Bak is termed BakΔ3, represents amino acids 96-210 of full-length Bak and is shown in FIG. 3. BakΔ3 was cloned into a baculovirus vector. The PCR amplified BakΔ3 was subcloned into the pBlueBac III vector (Invitrogen) and recombinant plasmids were isolated. Recombinants were sequenced by the dideoxy chain termination method (Sanger et al. (1977) Proc. Natl. Acad. Sci. USA 74:5463-5467) using sequencing kits purchased from U.S. Biochemicals (SEQUENASE® version 2.0). Recombinant viruses were generated by cotransfecting *Spodoptera frugiperda* clone 9 (Sf9) cells with the recombinant plasmid and wild-type AcMNPV viral DNA using cationic liposomes as described by supplier (Invitrogen). Recombinant viruses were identified by visual screening and PCR and propagation of recombinant baculovirus was performed as described by the supplier (Invitrogen).

For the production of recombinant BakΔ3, 1×10⁷ Sf9 cells were cultured in each of twenty 75 cm² tissue culture flasks (Corning) containing 15 ml of Grace's complete insect cell media (Invitrogen) supplemented with 10% fetal bovine serum. After allowing the insect cells to attach to the plate for 1 hour, the cells were infected at a multiplicity of infection of 5 with baculovirus expressing bakΔ3. The plates were placed on a rocker for 1 hour and then the media was removed and replaced with 15 ml of fresh media. The plates were placed at 27° C. and left for 72 hours. After allowing the Sf9 cells to express the BakΔ3, the cells were harvested, centrifuged, and washed with 1×PBS. The pellet was collected into a single 15 ml tube and washed again with 1×PBS. The pellet was then extracted with 0.5% NP-40 extraction buffer (10 mM HEPES, 142.5 mM KCl, 1 mM EGTA, 5 mM $MgCl_2$, 0.5% NP-40, pH 7.2). This was left overnight at 4° C. with gentle shaking.

The solubilized cell extract was then sonicated, centrifuged, and one ml of each supernatant was mixed with 50 ml of a suspension of glutathione SEPHAROSE® to which either gst, gst-BBP-L1 or gst-BBP-L2 was bound. The extract containing BakΔ3 was kept at 4° C. for 24 hours with the SEPHAROSE®-bound gst, gst-BBP-L1 or gst-BBP-L2 suspensions. The SEPHAROSE®-protein complexes were collected by centrifugation, washed three times with the buffer described above, then suspended in 100 ml each of 1×SDS-PAGE buffer. Eight μL of each sample were run on a 15% SDS PAGE gel and, after the proteins were satisfactorily separated, transferred to nitrocellulose for immunoblotting. Complexes containing the Bak derivative were detected using rabbit IgG anti-Bak antibodies and the blot was developed using enhanced chemiluminescence (ECL) and anti-rabbit IgG/peroxidase conjugate. The results, shown in FIG. 8B, indicate that N-terminal deletion of Bak represented by BakΔ3 is capable of interaction with BBP-L1, but is not capable of associating with the hydrophilic region represented by BBP-L2.

Example 6

Drug Screening Assay

This example describes an assay useful for screening for agents such as drugs that alter the affinity of binding of Bak with BBP.

Specifically, this example presents a scheme for using a BBP such as the BBP-Loop1 or BBP-Loop2 in a drug screening assay that is suitable for automated high through-put random drug screening. A DNA sequence encoding BBP-Loop1 or BBP-Loop2 is amplified by PCR and subcloned into the pGEX-5X plasmid in frame with gst, allowing the production of Gst-BBP-L1 or Gst-BBP-L2 fusion proteins in *E. coli*. Gst-BBP-L1 or Gst-BBP-L2 are purified by standard methods using glutathione-Sepharose chromatography, then the fusion proteins are immobilized onto 96-well microtiter plates. Bak coupled to a second moiety that can serve as a detectable tag, e.g. green fluorescent protein (GFP; Prasher (1995) *Trends Genet.* 11:320-323), is added along with the agent whose ability to affect the binding between Bak and BBP is to be tested, including, but not limited to a small molecule or peptide. Control samples include no test agent. After a suitable incubation period, the test wells are washed, and fluorescence is monitored by measuring excitation at 488 nm and emission at 511 nm. Test wells showing a significantly higher or significantly lower fluorescence compared with the control are then examined further to confirm an effect on Bak-BBP binding.

Example 7

Analysis of Bak-BBP Interaction

To further confirm Bak-BBP interactions and to determine regions of Bak that are important in binding to BBP, SPOTS peptide binding assays were performed.

Sixty-three Bak peptides, 15 amino acids in length, were synthesized on a membrane using a SPOTs kit according to suppliers instructions (Genosys Biotechnologies, The Woodlands, Tex.). The peptides were overlapping, off register by 4 amino acids, and spanned amino acids 1-194 (see SEQ ID NO: 2). All regions of Bak were represented except for the transmembrane region. The order of synthesis was determined using the SPOTscan and SPOTslot programs provided by the suppliers.

SPOTs kit included proprietary membrane for peptide synthesis, derivatized amino acids, computer program for determining the order of synthesis, synthesis trough, 10× blocking buffer concentrate, and complete instructions. Some reagents had to be obtained from outside sources. Dimethylformamide (DMF) was from EM Science (Gibbstown, N.J.) while N-methylpyrrolidone (NMP) was from Applied Biosystems (Foster City, Calif.). Both were peptide synthesis grade. Molecular Sieves (4 Å) were obtained from Aldrich (Milwaukee, Wis.).

Prior to the start of peptide synthesis, the solvents used (DMF and NMP) had to be further purified to remove any reactive amines or water. This was done using the molecular sieves which were activated by heating at 250° C. for 24 hours, followed by drying in a vacuum dessicator containing DRIERITE® dessicant (Aldrich) for another 48 hours. The activated sieves were mixed with the solvents (at 25% of the total solvent volume) and left for 72 hours.

Upon completion of peptide synthesis the membrane was washed in TBS (50 mM Tris, 150 mM NaCl, 5 mM KCl, pH 8) three times and then incubated in blocking buffer overnight (suppliers blocking buffer in TBS/0.05% TWEEN-20® (polysorbate 20), 5% sucrose) at room temperature. The membrane was washed three times with TBS/0.05% TWEEN-20® (polysorbate 20) and incubated overnight at room temperature in 25 mL of blocking buffer containing 2 mg purified GST-BBP loop 1, GST-BBP loop 2 or GST (negative control). The membrane was again washed three times with TBS/0.05% TWEEN-20® (polysorbate 20), incubated with rabbit polyclonal anti-GST (1:1000; Pharmacia) for 1 hour at room temperature, washed again with TBS/0.05% TWEEN-20® (polysorbate 20) and incubated with goat anti-rabbit IgG/peroxidase conjugate (Sigma, St. Louis, Mo.) for 1 hour at room temperature. The membrane was then developed using ECL method (Amersham, Chicago, Ill.).

The results were as follows. BBP loop1 interacted most strongly with two contiguous clusters of Bak peptides (FIG. 9). The first cluster overlapped the Bak BH3 domain (six peptides spanning amino acids 70 to 102) and the second cluster began upstream and extended into the N-terminal region of the BH1 domain (amino acids 103-126). Several weaker interactions occurred between BBP loop 1 and Bak peptides in two regions upstream of the Bak BH3 domain and a region between the Bak BH1 and BH2 domains. BBP loop 2 did not interact with any of the Bak peptides in the SPOTS assay (data not shown).

Figures 8A, 8B:
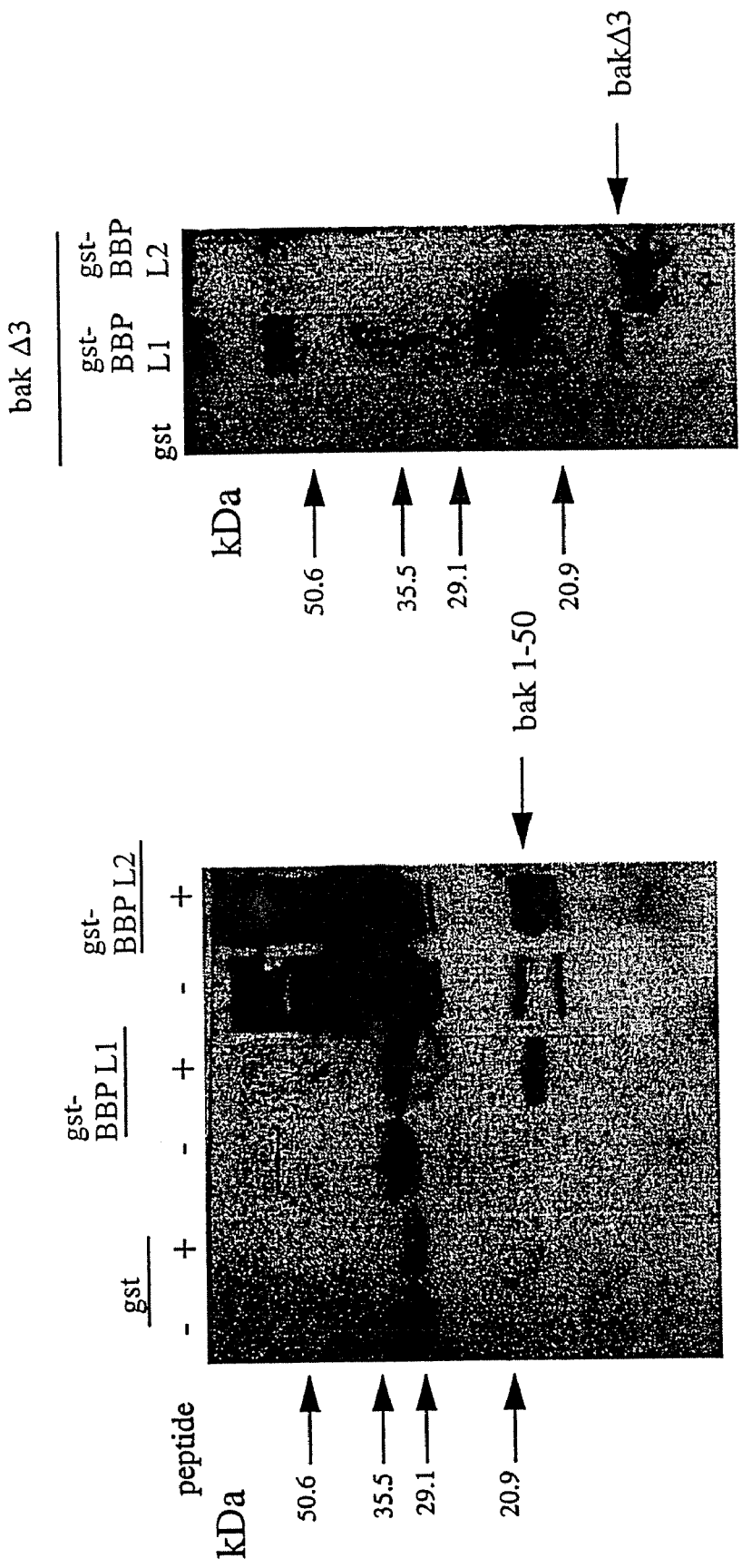
FIG. 8 shows the results of Western blot analysis of the interactions between BBP-Loop1, BBP-Loop2 and the Bak derivatives Bak 1-50 (FIG. 8A) and BakΔ3 (FIG. 8B).

The BH3 domain of Bak has been shown to be important for the cell death promoting activity of Bak (Chittenden et al., 1995 *EMBO J.* 14, 5589-5596). Our SPOTS data suggest that BBP can cooperate with Bak in modulating apoptosis by binding to the BH3 domain of Bak. Interestingly, it was recently shown that in some cases Bak does not require its BH3 domain to promote apoptosis (Simonian et al., 1997, *Oncogene* 15, 1871-1875). BakΔ3, a construct which lacks the N-terminal 95 amino acids, including the BH3 domain, was shown to be extremely active in promoting cell death in insect cells (data not shown). BakΔ3 was also shown to bind to BBP loop 1 (FIG. 8B).

Our SPOTS data support that the BBP interaction with BakΔ3 occurs in the region of Bak upstream and extending into the N-terminal region of the BH1 domain (amino acids 103-126 of SEQ ID NO:2, defined as "BBP Binding Domain 1", nucleic acids 507-578 of SEQ ID NO:1, defined as "bbpbd-1") and also in the region immediately downstream from the BH1 domain (amino acids 138-156 of SEQ ID NO:2, defined as "BBP Binding Domain 2", nucleic acids 611-668 of SEQ ID NO:1, defined as "bbpbd-2"). Collectively, BBP Binding Domains 1 and 2 are defined as "BBP Binding Domains". The results support that these regions are additional important death domains of Bak.

Although the foregoing invention has been described in some detail for purposes of clarity and understanding, it will be apparent to those skilled in the art that certain changes and modifications can be practiced. Therefore, the description and examples should not be construed as limiting the scope of the invention, which is delineated by the appended claims.

The invention claimed is:

1. A method of increasing or decreasing apoptosis-induced cell death comprising increasing or decreasing the level of Bak Binding Protein (BBP) in a eukaryotic cell, the method comprising
transfecting the cell ex vivo with a recombinant nucleic acid molecule comprising an isolated polynucleotide selected from the group consisting of:
a) a polynucleotide comprising a nucleotide sequence encoding the polypeptide of SEQ ID NO:7;
b) a polynucleotide consisting of a nucleotide sequence encoding a fragment of SEQ ID NO:7, wherein the fragment consists of at least six linear amino acid residues of SEQ ID NO:7, and wherein the fragment binds to a Bak protein; and
c) a polynucleotide consisting of the full complement of the nucleotide sequence of (a) or (b),
wherein expression of the polynucleotide in the cell increases or decreases the level of BBP in the cell and thereby increases or decreases apoptosis-induced cell death.

2. The method of claim 1, wherein the fragment comprises a linear sequence of at least six amino acid residues of positions 1-42 of SEQ ID NO:7, or a linear sequence of at least six amino acid residues of positions 86-133 of SEQ ID NO:7, and wherein the fragment binds to a Bak protein.

3. The method of claim 1, wherein the fragment comprises a linear sequence of at least 12 amino acid residues of positions 1-42 of SEQ ID NO:7, or a linear sequence of at least 12 amino acid residues of positions 86-133 of SEQ ID NO:7.

4. The method of claim 1, wherein the fragment comprises a linear sequence of at least 18 amino acid residues of positions 1-42 of SEQ ID NO:7, or a linear sequence of at least 18 amino acid residues of positions 86-133 of SEQ ID NO:7.

5. The method of claim 1, wherein the fragment comprises a linear sequence of at least 25 amino acid residues of positions 1-42 of SEQ ID NO:7, or a linear sequence of at least 25 amino acid residues of positions 86-133 of SEQ ID NO:7.

6. The method of claim 1, wherein the fragment comprises positions 1-42 of SEQ ID NO:7, or positions 86-133 of SEQ ID NO:7.

7. The method of claim 1, wherein the fragment comprises positions 1-42 of SEQ ID NO:7.

8. The method of claim 1, wherein the fragment comprises positions 86-133 of SEQ ID NO:7.

9. The method of claim 1, wherein the polynucleotide encodes the polypeptide of SEQ ID NO:7.

10. The method of claim 1, wherein the polynucleotide comprises a nucleotide sequence of SEQ ID NO:6.

11. The method of claim 1, wherein the polynucleotide consists of a fragment of SEQ ID NO:6, wherein the fragment consists of at least 18 nucleotides of SEQ ID NO:6, wherein the polynucleotide encodes a protein that binds to a Bak protein.

12. The method of claim 1, wherein the BBP levels are increased by expression of the recombinant nucleic acid molecule comprising the nucleotide sequence encoding SEQ ID NO:7 or the fragment of SEQ ID NO:7.

13. The method of claim 1, wherein the BBP levels are decreased by decreasing expression of an endogenous BBP gene, wherein the recombinant nucleic acid molecule comprises the nucleotide sequence that is the full complement of the nucleotide sequence encoding SEQ ID NO:7 or the full complement of the fragment of SEQ ID NO:7.

14. The method of claim 1, wherein expression of the recombinant nucleic acid molecule is under the control of an inducible promoter.

15. The method of claim 1, wherein the recombinant nucleic acid molecule is transfected into cells ex vivo and further comprising the steps of reintroducing the transfected cells into a non-human animal.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 2094 base pairs
      (B) TYPE: nucleic acid
      (C) STRANDEDNESS: double
      (D) TOPOLOGY: linear (ix) FEATURE:
      (A) NAME/KEY: CDS
      (B) LOCATION: 201..833

(xi) SEQUENCE DESCRIPTION: SEQ ID NO: 1:

```
GAGGATCTAC AGGGGACAAG TAAAGGCTAC ATCCAGATGC CGGGAATGCA CTGACGCCCA         60

TTCCTGGAAA CTGGGCTCCC ACTCAGCCCC TGGGAGCAGC AGCCGCCAGC CCCTCGGACC        120

TCCATCTCCA CCCTGCTGAG CCACCCGGGT TGGGCCAGGA TCCCGGCAGG CTGATCCCGT        180

CCTCCACTGA GACCTGAAAA ATG GCT TCG GGG CAA GGC CCA GGT CCT CCC           230
                      Met Ala Ser Gly Gln Gly Pro Gly Pro Pro
                       1               5                  10

AGG CAG GAG TGC GGA GAG CCT GCC CTG CCC TCT GCT TCT GAG GAG CAG         278
Arg Gln Glu Cys Gly Glu Pro Ala Leu Pro Ser Ala Ser Glu Glu Gln
             15                  20                  25

GTA GCC CAG GAC ACA GAG GAG GTT TTC CGC AGC TAC GTT TTT TAC CGC         326
Val Ala Gln Asp Thr Glu Glu Val Phe Arg Ser Tyr Val Phe Tyr Arg
         30                  35                  40

CAT CAG CAG GAA CAG GAG GCT GAA GGG GTG GCT GCC CCT GCC GAC CCA         374
His Gln Gln Glu Gln Glu Ala Glu Gly Val Ala Ala Pro Ala Asp Pro
             45                  50                  55

GAG ATG GTC ACC TTA CCT CTG CAA CCT AGC AGC ACC ATG GGG CAG GTG         422
Glu Met Val Thr Leu Pro Leu Gln Pro Ser Ser Thr Met Gly Gln Val
     60                  65                  70

GGA CGG CAG CTC GCC ATC ATC GGG GAC GAC ATC AAC CGA CGC TAT GAC         470
Gly Arg Gln Leu Ala Ile Ile Gly Asp Asp Ile Asn Arg Arg Tyr Asp
 75                  80                  85                  90

TCA GAG TTC CAG ACC ATG TTG CAG CAC CTG CAG CCC ACG GCA GAG AAT         518
Ser Glu Phe Gln Thr Met Leu Gln His Leu Gln Pro Thr Ala Glu Asn
                 95                 100                 105

GCC TAT GAG TAC TTC ACC AAG ATT GCC ACC AGC CTG TTT GAG AGT GGC         566
Ala Tyr Glu Tyr Phe Thr Lys Ile Ala Thr Ser Leu Phe Glu Ser Gly
             110                 115                 120

ATC AAT TGG GGC CGT GTG GTG GCT CTT CTG GGC TTC GGC TAC CGT CTG         614
Ile Asn Trp Gly Arg Val Val Ala Leu Leu Gly Phe Gly Tyr Arg Leu
```

```
                       125                 130                 135
GCC CTA CAC GTC TAC CAG CAT GGC CTG ACT GGC TTC CTA GGC CAG GTG        662
Ala Leu His Val Tyr Gln His Gly Leu Thr Gly Phe Leu Gly Gln Val
         140                 145                 150

ACC CGC TTC GTG GTC GAC TTC ATG CTG CAT CAC TGC ATT GCC CGG TGG        710
Thr Arg Phe Val Val Asp Phe Met Leu His His Cys Ile Ala Arg Trp
155                 160                 165                 170

ATT GCA CAG AGG GGT GGC TGG GTG GCA GCC CTG AAC TTG GGC AAT GGT        758
Ile Ala Gln Arg Gly Gly Trp Val Ala Ala Leu Asn Leu Gly Asn Gly
                175                 180                 185

CCC ATC CTG AAC GTG CTG GTG GTT CTG GGT GTG GTT CTG TTG GGC CAG        806
Pro Ile Leu Asn Val Leu Val Val Leu Gly Val Val Leu Leu Gly Gln
            190                 195                 200

TTT GTG GTA CGA AGA TTC TTC AAA TCA TGACTCCCAA GGGTGCCCTT              853
Phe Val Val Arg Arg Phe Phe Lys Ser
            205                 210

TGGGTCCCGG TTCAGACCCC TGCCTGGACT TAAGCGAAGT CTTTGCCTTC TCTGTTCCCT       913

TGCAGGGTCC CCCCTCAAGA GTACAGAAGC TTTAGCAAGT GTGCACTCCA GCTTCGGAGG       973

CCCTGCGTGG GGGCCAGTCA GGCTGCAGAG GCACCTCAAC ATTGCATGGT GCTAGTGCCC      1033

TCTCTCTGGG CCCAGGGCTG TGGCCGTCTC CTCCCTCAGC TCTCTGGGAC CTCCTTAGCC      1093

CTGTCTGCTA GGCGCTGGGG AGACTGATAA CTTGGGGAGG CAAGAGACTG GGAGCCACTT      1153

CTCCCCAGAA AGTGTTTAAC GGTTTTAGCT TTTTATAATA CCCTTGTGAG AGCCCATTCC      1213

CACCATTCTA CCTGAGGCCA GGACGTCTGG GGTGTGGGGA TTGGTGGGTC TATGTTCCCC      1273

AGGATTCAGC TATTCTGGAA GATCAGCACC CTAAGAGATG GGACTAGGAC CTGAGCCTGG      1333

TCCTGGCCGT CCCTAAGCAT GTGTCCCAGG AGCAGGACCT ACTAGGAGAG GGGGGCCAAG      1393

GTCCTGCTCA ACTCTACCCC TGCTCCCATT CCTCCCTCCG GCCATACTGC CTTTGCAGTT      1453

GGACTCTCAG GGATTCTGGG CTTGGGGTGT GGGGTGGGGT GGAGTCGCAG ACCAGAGCTG      1513

TCTGAACTCA CGTGTCAGAA GCCTCCAAGC CTGCCTCCCA AGGTCCTCTC AGTTCTCTCC      1573

CTTCCTCTCT CCTTATAGAC ACTTGCTCCC AACCCATTCA CTACAGGTGA AGGCTCTCAC      1633

CCATCCCTGG GGGCCTTGGG TGAGTGGCCT GCTAAGGCTC CTCCTTGCCC AGACTACAGG      1693

GCTTAGGACT TGGTTTGTTA TATCAGGGAA AAGGAGTAGG GAGTTCATCT GGAGGGTTCT      1753

AAGTGGGAGA AGGACTATCA ACACCACTAG GAATCCCAGA GGTGGATCCT CCCTCATGGC      1813

TCTGGCACAG TGTAATCCAG GGGTGTAGAT GGGGGAACTG TGAATACTTG AACTCTGTTC      1873

CCCCACCCTC CATGCTCCTC ACCTGTCTAG GTCTCCTCAG GGTGGGGGGT GACAGTGCCT      1933

TCTCTATTGG CACAGCCTAG GGTCTTGGGG GTCAGGGGGG AGAAGTTCTT GATTCAGCCA      1993

AATGCAGGGA GGGGAGGCAG ATGGAGCCCA TAGGCCACCC CCTATCCTCT GAGTGTTTGG      2053

AAATAAACTG TGCAATCCCC TCAAAAAAAA AACGGAGATC C                         2094

(2) INFORMATION FOR SEQ ID NO: 2:

(i) SEQUENCE CHARACTERISTICS:
        (A) LENGTH: 211 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Ser Gly Gln Gly Pro Gly Pro Pro Arg Gln Glu Cys Gly Glu
 1               5                  10                  15
```

```
Pro Ala Leu Pro Ser Ala Ser Glu Glu Gln Val Ala Gln Asp Thr Glu
            20                  25                  30
Glu Val Phe Arg Ser Tyr Val Phe Tyr Arg His Gln Gln Glu Gln Glu
        35                  40                  45
Ala Glu Gly Val Ala Ala Pro Ala Asp Pro Glu Met Val Thr Leu Pro
    50                  55                  60
Leu Gln Pro Ser Ser Thr Met Gly Val Gly Arg Gln Leu Ala Ile
65                  70                  75                  80
Ile Gly Asp Asp Ile Asn Arg Arg Tyr Asp Ser Glu Phe Gln Thr Met
                85                  90                  95
Leu Gln His Leu Gln Pro Thr Ala Glu Asn Ala Tyr Glu Tyr Phe Thr
            100                 105                 110
Lys Ile Ala Thr Ser Leu Phe Glu Ser Gly Ile Asn Trp Gly Arg Val
        115                 120                 125
Val Ala Leu Leu Gly Phe Gly Tyr Arg Leu Ala Leu His Val Tyr Gln
    130                 135                 140
His Gly Leu Thr Gly Phe Leu Gly Gln Val Thr Arg Phe Val Val Asp
145                 150                 155                 160
Phe Met Leu His His Cys Ile Ala Arg Trp Ile Ala Gln Arg Gly Gly
                165                 170                 175
Trp Val Ala Ala Leu Asn Leu Gly Asn Gly Pro Ile Leu Asn Val Leu
            180                 185                 190
Val Val Leu Gly Val Val Leu Leu Gly Gln Phe Val Val Arg Arg Phe
        195                 200                 205
Phe Lys Ser
    210

(2) INFORMATION FOR SEQ ID NO: 3:

(i) SEQUENCE CHARACTERISTICS:
        (A) LENGTH: 2094 base pairs
        (B) TYPE: nucleic acid
        (C) STRANDEDNESS: double
        (D) TOPOLOGY: linear (iv) ANTI-SENSE: YES (xi) SEQUENCE DESCRIPTION: SEQ ID NO: 3:

GGATCTCCGT TTTTTTTTTG AGGGGATTGC ACAGTTTATT TCCAAACACT CAGAGGATAG     60

GGGGTGGCCT ATGGGCTCCA TCTGCCTCCC CTCCCTGCAT TTGGCTGAAT CAAGAACTTC    120

TCCCCCCTGA CCCCCAAGAC CATAGGCTGT GCCAATAGAA AAGGCACTGT CACCCCCCAC    180

CCTGAGGAGA CCTAGACAGG TGAGGAGCAT GGAGGGTGGG GGAACAGAGT TCAAGTATTC    240

ACAGTTCCCC CATCTACACC CCTGGATTAC ACTGTGCCAG AGCCATGAGG GAGGATCCAC    300

CTCTGGGATT CCTAGTGGTG TTGATAGTCC TTCTCCCACT TAGAACCCTC CAGATGAACT    360

CCCTACTCCT TTTCCCTGAT ATAACAAACC AAGTCCTAAG CCCTGTAGTC TGGGCAAGGA    420

GGAGCCTTAG CAGGCCACTC ACCCAAGGCC CCCAGGGATG GGTGAGAGCC TTCACCTGTA    480

GTGAATGGGT TGGGAGCAAG TGTCTATAAG GAGAGAGGAA GGGAGAGAAC TGAGAGGACC    540

TTGGGAGGCA GGCTTGGAGG CTTCTGACAC GTGAGTTCAG ACAGCTCTGG TCTGCGACTC    600

CACCCCACCC CACACCCCAA GCCCAGAATC CCTGAGAGTC CAACTGCAAA GGCAGTATGG    660

CCGGAGGGAG GAATGGGAGC AGGGGTAGAG TTGAGCAGGA CCTTGGCCCC CCTCTCCTAG    720

TAGGTCCTGC TCCTGGGACA CATGCTTAGG GACGGCCAGG ACCAGGCTCA GGTCCTAGTC    780

CCATCTCTTA GGGTGCTGAT CTTCCAGAAT AGCTGAATCC TGGGGAACAT AGACCCACCA    840
```

```
ATCCCCACAC CCCAGACGTC CTGGCCTCAG GTAGAATGGT GGGAATGGGC TCTCACAAGG      900

GTATTATAAA AAGCTAAAAC CGTTAAACAC TTTCTGGGGA GAAGTGGCTC CCAGTCTCTT      960

GCCTCCCCAA GTTATCAGTC TCCCCAGCGC CTAGCAGACA GGGCTAAGGA GGTCCCAGAG     1020

AGCTGAGGGA GGAGACGGCC ACAGCCCTGG GCCCAGAGAG AGGGCACTAG CACCATGCAA     1080

TGTTGAGGTG CCTCTGCAGC CTGACTGGCC CCCACGCAGG GCCTCCGAAG CTGGAGTGCA     1140

CACTTGCTAA AGCTTCTGTA CTCTTGAGGG GGGACCCTGC AAGGGAACAG AGAAGGCAAA     1200

GACTTCGCTT AAGTCCAGGC AGGGGTCTGA ACCGGGACCC AAAGGGCACC CTTGGGAGTC     1260

ATGATTTGAA GAATCTTCGT ACCACAAACT GGCCCAACAG AACCACACCC AGAACCACCA     1320

GCACGTTCAG GATGGGACCA TTGCCCAAGT TCAGGGCTGC CACCCAGCCA CCCCTCTGTG     1380

CAATCCACCG GGCAATGCAG TGATGCAGCA TGAAGTCGAC CACGAAGCGG GTCACCTGGC     1440

CTAGGAAGCC AGTCAGGCCA TGCTGGTAGA CGTGTAGGGC CAGACGGTAG CCGAAGCCCA     1500

GAAGAGCCAC CACACGGCCC CAATTGATGC CACTCTCAAA CAGGCTGGTG GCAATCTTGG     1560

TGAAGTACTC ATAGGCATTC TCTGCCGTGG GCTGCAGGTG CTGCAACATG GTCTGGAACT     1620

CTGAGTCATA GCGTCGGTTG ATGTCGTCCC CGATGATGGC GAGCTGCCGT CCCACCTGCC     1680

CCATGGTGCT GCTAGGTTGC AGAGGTAAGG TGACCATCTC TGGGTCGGCA GGGGCAGCCA     1740

CCCCTTCAGC CTCCTGTTCC TGCTGATGGC GGTAAAAAAC GTAGCTGCGG AAAACCTCCT     1800

CTGTGTCCTG GGCTACCTGC TCCTCAGAAG CAGAGGGCAG GGCAGGCTCT CCGCACTCCT     1860

GCCTGGGAGG ACCTGGGCCT TGCCCCGAAG CCATTTTTCA GGTCTCAGTG GAGGACGGGA     1920

TCAGCCTGCC GGGATCCTGG CCCAACCCGG GTGGCTCAGC AGGGTGGAGA TGGAGGTCCG     1980

AGGGGCTGGC GGCTGCTGCT CCCAGGGGCT GAGTGGGAGC CCAGTTTCCA GGAATGGGCG     2040

TCAGTGCATT CCCGGCATCT GGATGTAGCC TTTACTTGTC CCCTGTAGAT CCTC           2094
```

(2) INFORMATION FOR SEQ ID NO:4:
    /note= "Bak (delta)2 (delta)TM"

(i) SEQUENCE CHARACTERISTICS:
        (A) LENGTH: 117 amino acids
        (B) TYPE: amino acid
        (C) STRANDEDNESS: single
        (D) TOPOLOGY: linear (ix) FEATURE:
        (A) NAME/KEY: Protein
        (B) LOCATION: 1..117

(xi) SEQUENCE DESCRIPTION: SEQ ID NO: 4:

```
Met Gly Gln Val Gly Arg Gln Leu Ala Ile Ile Gly Asp Asp Ile Asn
1               5                  10                  15

Arg Arg Tyr Asp Ser Glu Phe Gln Thr Met Leu Gln His Leu Gln Pro
            20                  25                  30

Thr Ala Glu Asn Ala Tyr Glu Tyr Phe Thr Lys Ile Ala Thr Ser Leu
        35                  40                  45

Phe Glu Ser Gly Ile Asn Trp Gly Arg Val Val Ala Leu Leu Gly Phe
    50                  55                  60

Gly Tyr Arg Leu Ala Leu His Val Tyr Gln His Gly Leu Thr Gly Phe
65                  70                  75                  80

Leu Gly Gln Val Thr Arg Phe Val Val Asp Phe Met Leu His Cys
                85                  90                  95

Ile Ala Arg Trp Ile Ala Gln Arg Gly Gly Trp Val Ala Ala Leu Asn
            100                 105                 110
```

```
Leu Gly Asn Gly Pro
        115

(2) INFORMATION FOR SEQ ID NO: 5:

(i) SEQUENCE CHARACTERISTICS:
        (A) LENGTH: 116 amino acids
        (B) TYPE: amino acid
        (C) STRANDEDNESS: single
        (D) TOPOLOGY: linear (ix) FEATURE:
        (A) NAME/KEY: Protein
        (B) LOCATION: 1..116
        (D) OTHER INFORMATION: /note= "Bak (delta)3"

(xi) SEQUENCE DESCRIPTION: SEQ ID NO: 5:

Met Leu Gln His Leu Gln Pro Thr Ala Glu Asn Ala Tyr Glu Tyr Phe
1               5                   10                  15

Thr Lys Ile Ala Thr Ser Leu Phe Glu Ser Gly Ile Asn Trp Gly Arg
            20                  25                  30

Val Val Ala Leu Leu Gly Phe Gly Tyr Arg Leu Ala Leu His Val Tyr
        35                  40                  45

Gln His Gly Leu Thr Gly Phe Leu Gly Gln Val Thr Arg Phe Val Val
    50                  55                  60

Asp Phe Met Leu His His Cys Ile Ala Arg Trp Ile Ala Gln Arg Gly
65                  70                  75                  80

Gly Trp Val Ala Ala Leu Asn Leu Gly Asn Gly Pro Ile Leu Asn Val
                85                  90                  95

Leu Val Val Leu Gly Val Val Leu Leu Gly Gln Phe Val Val Arg Arg
            100                 105                 110

Phe Phe Lys Ser
        115

(2) INFORMATION FOR SEQ ID NO: 6:

(i) SEQUENCE CHARACTERISTICS:
        (A) LENGTH: 975 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 26..478

(xi) SEQUENCE DESCRIPTION: SEQ ID NO: 6:

GTCCTCGCGA GACAAGCTCA CCGAA ATG GCC GCG TCC AGT CAA GGA AAC TTT        52
                           Met Ala Ala Ser Ser Gln Gly Asn Phe
                               215                         220

GAG GGA AAT TTT GAG TCA CTG GAC CTT GCG GAA TTT GCT AAG AAG CAG       100
Glu Gly Asn Phe Glu Ser Leu Asp Leu Ala Glu Phe Ala Lys Lys Gln
                225                 230                 235

CCA TGG TGG CGT AAG CTG TTC GGG CAG GAA TCT GGA CCT TCA GCA GAA       148
Pro Trp Trp Arg Lys Leu Phe Gly Gln Glu Ser Gly Pro Ser Ala Glu
        240                 245                 250

AAG TAT AGC GTG GCA ACC CAG CTG TTC ATT GGA GGT GTC ACT GGA TGG       196
Lys Tyr Ser Val Ala Thr Gln Leu Phe Ile Gly Gly Val Thr Gly Trp
    255                 260                 265

TGC ACA GGT TTC ATA TTC CAG AAG GTT GGA AAG TTG GCT GCA ACA GCT       244
Cys Thr Gly Phe Ile Phe Gln Lys Val Gly Lys Leu Ala Ala Thr Ala
    270                 275                 280
```

```
GTG GGA GGT GGA TTT TTT CTC CTT CAG CTT GCA AAC CAT ACT GGG TAC     292
Val Gly Gly Gly Phe Phe Leu Leu Gln Leu Ala Asn His Thr Gly Tyr
285                 290                 295                 300

ATC AAA GTT GAC TGG CAA CGA GTG GAG AAG GAC ATG AAG AAA GCC AAA     340
Ile Lys Val Asp Trp Gln Arg Val Glu Lys Asp Met Lys Lys Ala Lys
                305                 310                 315

GAG CAG CTG AAG ATC CGT AAG AGC AAT CAG ATA CCT ACT GAG GTC AGG     388
Glu Gln Leu Lys Ile Arg Lys Ser Asn Gln Ile Pro Thr Glu Val Arg
            320                 325                 330

AGC AAA GCT GAG GAG GTG GTG TCA TTT GTG AAG AAG AAT GTT CTA GTA     436
Ser Lys Ala Glu Glu Val Val Ser Phe Val Lys Lys Asn Val Leu Val
        335                 340                 345

ACT GGG GGA TTT TTC GGA GGC TTT CTG CTT GGC ATG GCA TCC             478
Thr Gly Gly Phe Phe Gly Gly Phe Leu Leu Gly Met Ala Ser
    350                 355                 360

TAAGGAAGAT GACCTCATGT TCATTGTTCC TGGTTTTTTC CAGCCAGCAG CCTCTACACT    538

CCATCATAGG ACATCGAGTC CCTCCTCCTC TTCTCCCATG CCCTTCTTCC CTGCCATGGC    598

AAATCTGAGT GGCTTCTCTA AGCATCTGCT GGTACAAGTC AATGTGGCAC CATGAGCTTC    658

ATGGTGGCAG AAGAGACAAT AGTCCTTAGC TCTCCTCCCA GTACACCCCC TACTTGGCCA    718

GTCTGTAGGC CAACAAGAAG GTTCCTTTAC CCCCATGCAA GACACTTATG AGAACACATT    778

ACAAGATGGC TGACCGTGGA GGATGAGTGG ATCCTGAAAG GTTGTCCCAA ACTGTTGATT    838

TGGAAAAGAA ATAAGCACAT AGATAACCTT ATTGTGTGCT GCATGGAAAG GAAAGGAACT    898

GAATACATTT GCCTTTAAGC ATGAAAAAAA AAAAAAAAAA AAAAAAAAAA AAAAAAAAAA    958

AAAAAAAAG AAAAAA                                                    975

(2) INFORMATION FOR SEQ ID NO: 7:

(i) SEQUENCE CHARACTERISTICS:
        (A) LENGTH: 151 amino acids
        (B) TYPE: amino acid
        (D) TOPOLOGY: linear (ii) MOLECULE TYPE: protein (xi) SEQUENCE DESCRIPTION: SEQ ID NO: 7:

Met Ala Ala Ser Ser Gln Gly Asn Phe Glu Gly Asn Phe Glu Ser Leu
1               5                   10                  15

Asp Leu Ala Glu Phe Ala Lys Lys Gln Pro Trp Trp Arg Lys Leu Phe
                20                  25                  30

Gly Gln Glu Ser Gly Pro Ser Ala Glu Lys Tyr Ser Val Ala Thr Gln
            35                  40                  45

Leu Phe Ile Gly Gly Val Thr Gly Trp Cys Thr Gly Phe Ile Phe Gln
    50                  55                  60

Lys Val Gly Lys Leu Ala Ala Thr Ala Val Gly Gly Phe Phe Leu
65                  70                  75                  80

Leu Gln Leu Ala Asn His Thr Gly Tyr Ile Lys Val Asp Trp Gln Arg
                85                  90                  95

Val Glu Lys Asp Met Lys Lys Ala Lys Glu Gln Leu Lys Ile Arg Lys
                100                 105                 110

Ser Asn Gln Ile Pro Thr Glu Val Arg Ser Lys Ala Glu Glu Val Val
            115                 120                 125

Ser Phe Val Lys Lys Asn Val Leu Val Thr Gly Gly Phe Phe Gly Gly
        130                 135                 140
```

```
Phe Leu Leu Gly Met Ala Ser
145                 150
```